(12) United States Patent
Dhar et al.

(10) Patent No.: US 10,398,663 B2
(45) Date of Patent: Sep. 3, 2019

(54) MITOCHONDRIAL DELIVERY OF 3-BROMOPYRUVATE

(71) Applicant: UNIVERSITY OF GEORGIA RESEARCH FOUNDATION, INC., Athens, GA (US)

(72) Inventors: Shanta Dhar, Miami, FL (US); Sean Marrache, Portland, OR (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 0 days.

(21) Appl. No.: 15/123,786

(22) PCT Filed: Mar. 13, 2015

(86) PCT No.: PCT/US2015/020591
§ 371 (c)(1),
(2) Date: Sep. 6, 2016

(87) PCT Pub. No.: WO2015/138992
PCT Pub. Date: Sep. 17, 2015

(65) Prior Publication Data
US 2017/0014361 A1     Jan. 19, 2017

Related U.S. Application Data

(60) Provisional application No. 61/953,159, filed on Mar. 14, 2014.

(51) Int. Cl.
| | |
|---|---|
| A61K 31/19 | (2006.01) |
| A61K 41/00 | (2006.01) |
| A61N 5/06 | (2006.01) |
| A61K 31/194 | (2006.01) |
| A61K 31/416 | (2006.01) |
| A61K 31/7004 | (2006.01) |
| A61K 47/54 | (2017.01) |
| A61K 47/69 | (2017.01) |
| A61N 5/067 | (2006.01) |

(52) U.S. Cl.
CPC ............ *A61K 31/19* (2013.01); *A61K 31/194* (2013.01); *A61K 31/416* (2013.01); *A61K 31/7004* (2013.01); *A61K 41/0042* (2013.01); *A61K 41/0057* (2013.01); *A61K 47/54* (2017.08); *A61K 47/548* (2017.08); *A61K 47/6907* (2017.08); *A61K 47/6923* (2017.08); *A61N 5/062* (2013.01); *A61N 2005/067* (2013.01)

(58) Field of Classification Search
CPC .... A61K 31/19; A61K 31/194; A61K 31/416; A61K 31/7004; A61K 41/0042; A61K 41/0057; A61K 47/54; A61K 47/548; A61K 47/6907; A61K 47/6923; A61N 2005/067; A61N 5/062
See application file for complete search history.

(56) References Cited

U.S. PATENT DOCUMENTS

| | | |
|---|---|---|
| 4,239,757 A | 12/1980 | Bodor |
| 4,999,344 A | 3/1991 | Jett-Tilton et al. |
| 6,217,864 B1 | 4/2001 | Coffino et al. |
| 6,331,532 B1 * | 12/2001 | Murphy ................ A61K 31/66 514/100 |
| 6,753,154 B1 | 6/2004 | Chen et al. |
| 6,835,718 B2 | 12/2004 | Kosak |
| 7,329,638 B2 | 2/2008 | Yang et al. |
| 7,393,924 B2 | 7/2008 | Vitaliano et al. |
| 7,638,558 B2 | 12/2009 | Breitenkamp et al. |

(Continued)

FOREIGN PATENT DOCUMENTS

| | | |
|---|---|---|
| EP | 1995321 A2 | 11/2008 |
| EP | 2002714 A1 | 12/2008 |

(Continued)

OTHER PUBLICATIONS

Dykman et al. Gold nanoparticles in biomedical applications: recent advances and perspectives. Chem. Soc. Rev., 2012, 41:2256-2282.*
Jiang et al. A Mitochondria-Targeted Triphenylphosphonium-Conjugated Nitroxide Functions as a Radioprotector/Mitigator. Radiat Res. Dec. 2009; 172(6): 706-717. (Year: 2009).*
Reily et al. Mitochondrially targeted compounds and their impact on cellular bioenergetics. Redox Biology 1 (2013):86-93. (Year: 2013).*
Modica-Napolitano et al. Delocalized lipophilic cations selectively target the mitochondria of carcinoma cells. Advanced Drug Delivery Reviews 49 (2001) 63-70. (Year: 2001).*
Dykman et al. Gold nanoparticles in biomedical applications: recent advances and perspectives. Chem. Soc. Rev., 2012, 41, 2256-2282. (Year: 2012).*

(Continued)

*Primary Examiner* — Robert A Wax
*Assistant Examiner* — Olga V. Tcherkasskaya
(74) *Attorney, Agent, or Firm* — Mueting, Raasch & Gebhardt, P.A.

(57) ABSTRACT

A mitochondria targeted gold nanoparticle (T-3-BP-AuNP) decorated with 3-bromopyruvate (3-BP) and delocalized lipophilic triphenylphosphonium (TPP) cations to target the mitochondrial membrane potential ($\Delta\psi$m) was developed for delivery of 3-BP to cancer cell mitochondria by taking advantage of higher $\Delta\psi$m in cancer cell compared to normal cells. This construct showed remarkable anticancer activity in prostate cancer cells compared to non-targeted construct NT-3-BP-AuNP and free 3-BP. Anticancer activity of T-3-BP-AuNP was further enhanced upon laser irradiation by exciting the surface plasmon resonance band of AuNP and thereby utilizing a combination of 3-BP chemotherapeutic and AuNP photothermal effects. T-3-BP-AuNPs showed markedly enhanced ability to alter cancer cell metabolism by inhibiting glycolysis and demolishing mitochondrial oxidative phosphorylation in prostate cancer cells. Our findings demonstrated that mitochondria targeted and concerted chemo-photothermal treatment of glycolytic cancer cells with a single NP may have promise as a new anticancer therapy.

16 Claims, 12 Drawing Sheets

(56) References Cited

U.S. PATENT DOCUMENTS

| | | |
|---|---|---|
| 7,671,095 B2 | 3/2010 | Colson et al. |
| 7,725,169 B2 | 5/2010 | Boppart et al. |
| 7,728,036 B2 | 6/2010 | Huang et al. |
| 7,858,843 B2 | 12/2010 | Culbertson et al. |
| 7,871,596 B2 | 1/2011 | Kuniyoshi et al. |
| 7,931,902 B2 | 4/2011 | De Sauvage et al. |
| 7,935,782 B2 | 5/2011 | Harth et al. |
| 7,947,866 B2 | 5/2011 | Sparks |
| 7,956,237 B2 | 6/2011 | Montgomery et al. |
| 8,067,664 B2 | 11/2011 | Huang |
| 8,128,908 B2 | 3/2012 | Santra et al. |
| 8,178,527 B2 | 5/2012 | Chen et al. |
| 8,207,396 B2 | 6/2012 | Payne et al. |
| 8,221,480 B2 | 7/2012 | Boyden et al. |
| 8,227,661 B2 | 7/2012 | Edwards et al. |
| 8,256,233 B2 | 9/2012 | Boyden et al. |
| 8,263,663 B2 | 9/2012 | Sill et al. |
| 8,263,665 B2 | 9/2012 | Sill et al. |
| 8,273,373 B2 | 9/2012 | Alsberg et al. |
| 8,282,967 B2 | 10/2012 | Schoenfisch et al. |
| 8,297,959 B2 | 10/2012 | Larsen et al. |
| 8,299,128 B2 | 10/2012 | Sill et al. |
| 8,449,915 B1 | 5/2013 | Sung et al. |
| 8,574,544 B1 | 11/2013 | Sung et al. |
| 8,951,561 B2 * | 2/2015 | Vo-Dinh ............... A61K 39/00 424/489 |
| 2001/0021703 A1 | 9/2001 | Kosak |
| 2004/0038406 A1 | 2/2004 | Unger et al. |
| 2005/0025820 A1 | 2/2005 | Kester et al. |
| 2005/0042753 A1 | 2/2005 | Yang et al. |
| 2005/0153913 A1 | 7/2005 | Kosak |
| 2006/0040879 A1 | 2/2006 | Kosak |
| 2006/0228299 A1 | 10/2006 | Thorpe et al. |
| 2006/0240092 A1 | 10/2006 | Breitenkamp et al. |
| 2006/0292099 A1 | 12/2006 | Milburn et al. |
| 2007/0014833 A1 | 1/2007 | Milburn et al. |
| 2007/0066552 A1 | 3/2007 | Clarke et al. |
| 2007/0098713 A1 | 5/2007 | Unger et al. |
| 2007/0134340 A1 | 6/2007 | Prasad et al. |
| 2007/0141163 A1 | 6/2007 | Vitaliano et al. |
| 2007/0258889 A1 | 11/2007 | Douglas et al. |
| 2007/0269382 A1 | 11/2007 | Santra et al. |
| 2007/0292353 A1 * | 12/2007 | Levy ................... A61K 41/0071 424/9.34 |
| 2007/0292438 A1 | 12/2007 | Anderson et al. |
| 2007/0296099 A1 | 12/2007 | Larsen et al. |
| 2008/0051323 A1 | 2/2008 | Kosak |
| 2008/0069857 A1 | 3/2008 | Yeo et al. |
| 2008/0075718 A1 | 3/2008 | Colson et al. |
| 2008/0124344 A1 | 5/2008 | Combs et al. |
| 2008/0138277 A1 | 6/2008 | Epstein et al. |
| 2008/0160034 A1 | 7/2008 | Brennan et al. |
| 2008/0187487 A1 | 8/2008 | Larsen et al. |
| 2008/0206150 A1 | 8/2008 | Louie et al. |
| 2008/0243049 A1 | 10/2008 | Hardy |
| 2008/0253961 A1 | 10/2008 | Braden et al. |
| 2008/0294089 A1 | 11/2008 | Hardy |
| 2008/0299177 A1 | 12/2008 | Hardy |
| 2008/0299182 A1 | 12/2008 | Zhang et al. |
| 2008/0305106 A1 | 12/2008 | Zhang et al. |
| 2008/0311045 A1 | 12/2008 | Hardy |
| 2008/0311107 A1 | 12/2008 | Bollinger et al. |
| 2008/0312581 A1 | 12/2008 | Hardy |
| 2008/0319375 A1 | 12/2008 | Hardy |
| 2009/0018078 A1 | 1/2009 | Van Landingham, Jr. et al. |
| 2009/0022806 A1 | 1/2009 | Mousa et al. |
| 2009/0074828 A1 | 3/2009 | Alexis et al. |
| 2009/0092582 A1 | 4/2009 | Bogin et al. |
| 2009/0124534 A1 | 5/2009 | Reineke |
| 2009/0142348 A1 | 6/2009 | De Sauvage et al. |
| 2009/0148384 A1 | 6/2009 | Fischer et al. |
| 2009/0155349 A1 | 6/2009 | Heller et al. |
| 2009/0169521 A1 | 7/2009 | Levenberg et al. |
| 2009/0196876 A1 | 8/2009 | De Sauvage et al. |
| 2009/0214618 A1 | 8/2009 | Schoenfisch et al. |
| 2009/0288176 A1 | 11/2009 | Bollinger et al. |
| 2009/0293137 A1 | 11/2009 | Combs et al. |
| 2009/0306225 A1 | 12/2009 | Lichter et al. |
| 2009/0313707 A1 | 12/2009 | Combs et al. |
| 2010/0015050 A1 | 1/2010 | Panyam et al. |
| 2010/0015228 A1 | 1/2010 | Lichter et al. |
| 2010/0015263 A1 | 1/2010 | Lichter et al. |
| 2010/0016218 A1 | 1/2010 | Lichter et al. |
| 2010/0021416 A1 | 1/2010 | Lichter et al. |
| 2010/0022661 A1 | 1/2010 | Lichter et al. |
| 2010/0028994 A1 | 2/2010 | Desimone et al. |
| 2010/0031378 A1 | 2/2010 | Edwards et al. |
| 2010/0035341 A1 | 2/2010 | Itskovitz-Eldor et al. |
| 2010/0048736 A1 | 2/2010 | Liu et al. |
| 2010/0068141 A1 | 3/2010 | Kaushal et al. |
| 2010/0068806 A1 | 3/2010 | Laine et al. |
| 2010/0076018 A1 | 3/2010 | Liu et al. |
| 2010/0111837 A1 | 5/2010 | Boyden et al. |
| 2010/0111846 A1 | 5/2010 | Boyden et al. |
| 2010/0111847 A1 | 5/2010 | Boyden et al. |
| 2010/0111848 A1 | 5/2010 | Boyden et al. |
| 2010/0111849 A1 | 5/2010 | Boyden et al. |
| 2010/0111850 A1 | 5/2010 | Boyden et al. |
| 2010/0111854 A1 | 5/2010 | Boyden et al. |
| 2010/0111855 A1 | 5/2010 | Boyden et al. |
| 2010/0111938 A1 | 5/2010 | Boyden et al. |
| 2010/0112011 A1 | 5/2010 | Friedberg |
| 2010/0112067 A1 | 5/2010 | Boyden et al. |
| 2010/0112068 A1 | 5/2010 | Boyden et al. |
| 2010/0113614 A1 | 5/2010 | Boyden et al. |
| 2010/0114348 A1 | 5/2010 | Boyden et al. |
| 2010/0114547 A1 | 5/2010 | Boyden et al. |
| 2010/0119557 A1 | 5/2010 | Boyden et al. |
| 2010/0121466 A1 | 5/2010 | Boyden et al. |
| 2010/0113615 A1 | 6/2010 | Mulfinger et al. |
| 2010/0143243 A1 | 6/2010 | Boyden et al. |
| 2010/0144641 A1 | 6/2010 | Popel et al. |
| 2010/0152651 A1 | 6/2010 | Boyden et al. |
| 2010/0152880 A1 | 6/2010 | Boyden et al. |
| 2010/0159020 A1 | 6/2010 | Breitenkamp et al. |
| 2010/0163576 A1 | 7/2010 | Boyden et al. |
| 2010/0168900 A1 | 7/2010 | Boyden et al. |
| 2010/0185174 A1 | 7/2010 | Boyden et al. |
| 2010/0187728 A1 | 7/2010 | Boyden et al. |
| 2010/0196280 A1 | 8/2010 | Fischer et al. |
| 2010/0196481 A1 | 8/2010 | Pritchard et al. |
| 2010/0203142 A1 | 8/2010 | Zhang et al. |
| 2010/0215760 A1 | 8/2010 | Kundu et al. |
| 2010/0233153 A1 | 9/2010 | Borromeo et al. |
| 2010/0256232 A1 | 10/2010 | White et al. |
| 2010/0260706 A1 | 10/2010 | Bogin et al. |
| 2010/0273864 A1 | 10/2010 | Lichter et al. |
| 2010/0331819 A1 | 12/2010 | Hossainy et al. |
| 2011/0008304 A1 | 1/2011 | Troyer et al. |
| 2011/0008418 A1 * | 1/2011 | Ko ..................... A61K 31/202 424/450 |
| 2011/0008443 A1 | 1/2011 | Alsberg et al. |
| 2011/0020242 A1 | 1/2011 | Zheng et al. |
| 2011/0034422 A1 | 1/2011 | Kannan et al. |
| 2011/0027172 A1 * | 2/2011 | Wang ................. A61K 31/337 424/1.29 |
| 2011/0028172 A1 | 2/2011 | Wang et al. |
| 2011/0028181 A1 | 2/2011 | Byun et al. |
| 2011/0028395 A1 | 2/2011 | Popel et al. |
| 2011/0028945 A1 | 2/2011 | Amodei et al. |
| 2011/0038939 A1 | 2/2011 | Lvov et al. |
| 2011/0052715 A1 | 3/2011 | Davis et al. |
| 2011/0061114 A1 | 3/2011 | Edwards et al. |
| 2011/0091534 A1 | 4/2011 | Breitenkamp et al. |
| 2011/0092668 A1 | 4/2011 | Breitenkamp et al. |
| 2011/0093960 A1 | 4/2011 | Edwards et al. |
| 2011/0097330 A1 | 4/2011 | Horner et al. |
| 2011/0130325 A1 | 6/2011 | Labhasetwar |
| 2011/0142941 A1 | 6/2011 | Davis et al. |
| 2011/0150765 A1 | 6/2011 | Boyden et al. |
| 2011/0152305 A1 | 6/2011 | Colson et al. |
| 2011/0172826 A1 | 7/2011 | Amodei et al. |
| 2011/0173708 A1 | 7/2011 | Combs et al. |
| 2011/0182883 A1 | 7/2011 | Combs et al. |

(56) References Cited

U.S. PATENT DOCUMENTS

| | | |
|---|---|---|
| 2011/0191865 A1 | 8/2011 | Edwards et al. |
| 2011/0200579 A1 | 8/2011 | Cunningham et al. |
| 2011/0200677 A1 | 8/2011 | Chandran et al. |
| 2011/0203013 A1 | 8/2011 | Peterson et al. |
| 2011/0236389 A1* | 9/2011 | Ni .................. C07K 14/47 424/139.1 |
| 2011/0244048 A1 | 10/2011 | Amiji et al. |
| 2011/0245207 A1* | 10/2011 | Skulachev ......... A61K 31/352 514/130 |
| 2011/0252485 A1 | 10/2011 | De Sauvage et al. |
| 2011/0274620 A1 | 11/2011 | Harth et al. |
| 2011/0274747 A1 | 11/2011 | Habener et al. |
| 2011/0300532 A1* | 12/2011 | Jahnen-Dechent ........................ A61K 49/0423 435/6.1 |
| 2012/0005766 A1 | 1/2012 | Bollinger et al. |
| 2012/0015039 A1 | 1/2012 | Sexton et al. |
| 2012/0021036 A1* | 1/2012 | Majeti ................ A61K 9/1273 424/422 |
| 2012/0021055 A1 | 1/2012 | Schoenfisch et al. |
| 2012/0027681 A1 | 2/2012 | Jung et al. |
| 2012/0030776 A1 | 2/2012 | Combs et al. |
| 2012/0034169 A1 | 2/2012 | Schoenfisch et al. |
| 2012/0045389 A1 | 2/2012 | Gassull Duro et al. |
| 2012/0046346 A1 | 2/2012 | Rossi et al. |
| 2012/0058505 A1 | 3/2012 | Helms et al. |
| 2012/0101738 A1 | 4/2012 | Boyden et al. |
| 2012/0107365 A1 | 5/2012 | Colson et al. |
| 2012/0109613 A1 | 5/2012 | Boyden et al. |
| 2012/0128783 A1 | 5/2012 | Boyden et al. |
| 2012/0156499 A1 | 6/2012 | Torchilin et al. |
| 2012/0174239 A1 | 7/2012 | Anderson et al. |
| 2012/0177701 A1 | 7/2012 | Ilyinskii et al. |
| 2012/0184495 A1 | 7/2012 | Koyakutty et al. |
| 2012/0210450 A1 | 8/2012 | De Sauvage et al. |
| 2012/0232012 A1 | 9/2012 | Popel et al. |
| 2012/0263722 A1 | 10/2012 | Ghayur et al. |
| 2012/0263793 A1 | 10/2012 | Vitaliano |
| 2012/0272341 A1 | 10/2012 | Combs et al. |
| 2012/0276133 A1 | 11/2012 | Maldonado |
| 2012/0276134 A1 | 11/2012 | Fraser et al. |
| 2012/0276155 A1 | 11/2012 | Kishimoto et al. |
| 2012/0276157 A1 | 11/2012 | Fraser et al. |
| 2012/0276158 A1 | 11/2012 | Fraser et al. |
| 2012/0276159 A1 | 11/2012 | Fraser et al. |
| 2012/0276160 A1 | 11/2012 | Maldonado |
| 2013/0245357 A1* | 9/2013 | Chauhan ............ A61K 49/1845 600/12 |
| 2013/0280205 A1 | 10/2013 | Mozaffari et al. |
| 2014/0303081 A1 | 10/2014 | Dhar et al. |
| 2016/0022825 A1 | 1/2016 | Dhar et al. |
| 2017/0000740 A9 | 1/2017 | Dhar et al. |

FOREIGN PATENT DOCUMENTS

| | | |
|---|---|---|
| EP | 2050335 A1 | 4/2009 |
| EP | 2082645 A1 | 7/2009 |
| EP | 1907444 B1 | 8/2009 |
| EP | 1846355 B1 | 12/2009 |
| EP | 2186402 A1 | 5/2010 |
| EP | 2248903 A1 | 11/2010 |
| EP | 2430923 A1 | 3/2012 |
| JP | 2007/526907 A | 9/2007 |
| JP | 2008/297268 A | 12/2008 |
| WO | WO 2000/000503 A1 | 1/2000 |
| WO | WO 2000/045838 A1 | 8/2000 |
| WO | WO 2003/087021 A2 | 10/2003 |
| WO | WO 2003/103581 A2 | 12/2003 |
| WO | WO 2004/096140 A2 | 11/2004 |
| WO | WO 2005/019232 A1 | 3/2005 |
| WO | WO 2005/039534 A1 | 5/2005 |
| WO | WO 2005/058028 A2 | 6/2005 |
| WO | WO 2005/039534 A8 | 9/2005 |
| WO | WO 2005/079566 A2 | 9/2005 |
| WO | WO 2005/107818 A2 | 11/2005 |
| WO | WO 2005/112619 A2 | 12/2005 |
| WO | WO 2006/012201 A1 | 2/2006 |
| WO | WO 2006/026222 A2 | 3/2006 |
| WO | WO 2006/049854 A2 | 5/2006 |
| WO | WO 2006/079014 A2 | 7/2006 |
| WO | WO 2006/079120 A2 | 7/2006 |
| WO | WO 2006/098887 A2 | 9/2006 |
| WO | WO 2006/105403 A2 | 10/2006 |
| WO | WO 2006/107903 A2 | 10/2006 |
| WO | WO 2006/117675 A1 | 11/2006 |
| WO | WO 2006/127987 A2 | 11/2006 |
| WO | WO 2006/128121 A2 | 11/2006 |
| WO | WO 2006/132788 A2 | 12/2006 |
| WO | WO 2007/001962 A2 | 1/2007 |
| WO | WO 2007/014323 A2 | 2/2007 |
| WO | WO 2007/021423 A2 | 2/2007 |
| WO | WO 2007/033215 A2 | 3/2007 |
| WO | WO 2007/040469 A2 | 4/2007 |
| WO | WO 2007/080590 A2 | 7/2007 |
| WO | WO 2007/081608 A2 | 7/2007 |
| WO | WO 2007/101111 A2 | 9/2007 |
| WO | WO 2007/114979 A2 | 10/2007 |
| WO | WO 2007/120818 A2 | 10/2007 |
| WO | WO 2007/131128 A2 | 11/2007 |
| WO | WO 2007/133807 A2 | 11/2007 |
| WO | WO 2007/140483 A2 | 12/2007 |
| WO | WO 2008/013952 A2 | 1/2008 |
| WO | WO 2008/019357 A2 | 2/2008 |
| WO | WO 2008/036437 A2 | 3/2008 |
| WO | WO 2008/042469 A2 | 4/2008 |
| WO | WO 2008/048205 A2 | 4/2008 |
| WO | WO 2008/048288 A2 | 4/2008 |
| WO | WO 2008/051291 A2 | 5/2008 |
| WO | WO 2008/085828 A2 | 7/2008 |
| WO | WO 2008/087257 A1 | 7/2008 |
| WO | WO 2008/091465 A2 | 7/2008 |
| WO | WO 2008/091888 A2 | 7/2008 |
| WO | WO 2008/103409 A2 | 8/2008 |
| WO | WO 2008/106646 A2 | 9/2008 |
| WO | WO 2008/124632 A1 | 10/2008 |
| WO | WO 2008/127352 A2 | 10/2008 |
| WO | WO 2008/140507 A9 | 11/2008 |
| WO | WO 2008/143633 A2 | 11/2008 |
| WO | WO 2008/147481 A1 | 12/2008 |
| WO | WO 2009/009591 A9 | 1/2009 |
| WO | WO 2009/012303 A2 | 1/2009 |
| WO | WO 2009/023270 A2 | 2/2009 |
| WO | WO 2009/033130 A1 | 3/2009 |
| WO | WO 2009/046446 A2 | 4/2009 |
| WO | WO 2009/047587 A1 | 4/2009 |
| WO | WO 2009/073984 A1 | 6/2009 |
| WO | WO 2009/110939 A2 | 9/2009 |
| WO | WO 2009/132050 A2 | 10/2009 |
| WO | WO 2010/008995 A2 | 1/2010 |
| WO | WO 2010/011605 A2 | 1/2010 |
| WO | WO 2010/036961 A1 | 4/2010 |
| WO | WO 2010/042823 A1 | 4/2010 |
| WO | WO 2010/054264 A1 | 5/2010 |
| WO | WO 2010/054326 A2 | 5/2010 |
| WO | WO 2010/062413 A1 | 6/2010 |
| WO | WO 2010/074992 A2 | 7/2010 |
| WO | WO 2010/080557 A1 | 7/2010 |
| WO | WO 2010/083337 A2 | 7/2010 |
| WO | WO 2010/105058 A1 | 9/2010 |
| WO | WO 2010/111517 A1 | 9/2010 |
| WO | WO 2010/125115 A1 | 11/2010 |
| WO | WO 2010/143942 A1 | 12/2010 |
| WO | WO 2010/148007 A9 | 12/2010 |
| WO | WO 2011/082432 A1 | 7/2011 |
| WO | WO 2011/084620 A2 | 7/2011 |
| WO | WO 2011/109600 A1 | 9/2011 |
| WO | WO 2011/115602 A1 | 9/2011 |
| WO | WO 2011/119901 A1 | 9/2011 |
| WO | WO 2011/130624 A2 | 10/2011 |
| WO | WO 2011/133925 A2 | 10/2011 |
| WO | WO 2011/153348 A2 | 12/2011 |
| WO | WO 2012/061466 A2 | 5/2012 |
| WO | WO 2012/075337 A2 | 6/2012 |

(56) References Cited

FOREIGN PATENT DOCUMENTS

| WO | WO 2012/078745 A1 | 6/2012 |
|----|---|---|
| WO | WO 2012/092569 | 7/2012 |
| WO | WO 2012/106281 A2 | 8/2012 |
| WO | WO 2012/109466 A2 | 8/2012 |
| WO | WO 2012/135848 A2 | 10/2012 |
| WO | WO 2012/138570 A2 | 10/2012 |
| WO | WO 2012/142511 A2 | 10/2012 |
| WO | WO 2012/149252 A2 | 11/2012 |
| WO | WO 2012/149259 A1 | 11/2012 |
| WO | WO 2012/149265 A2 | 11/2012 |
| WO | WO 2012/149282 A2 | 11/2012 |
| WO | WO 2012/149301 A2 | 11/2012 |
| WO | WO 2012/149393 A9 | 11/2012 |
| WO | WO 2012/149405 A2 | 11/2012 |
| WO | WO 2012/149454 A2 | 11/2012 |
| WO | WO 2013/012628 A2 | 1/2013 |
| WO | WO 2013/033513 A1 | 3/2013 |
| WO | WO 2013/123298 A1 | 8/2013 |
| WO | WO 2014/059022 A1 | 4/2014 |
| WO | WO 2014/124425 A1 | 8/2014 |
| WO | WO 2014/169007 A2 | 10/2014 |
| WO | WO 2015/138992 A1 | 9/2015 |
| WO | WO 2016/022462 A1 | 2/2016 |

OTHER PUBLICATIONS

Ross et al. Rapid and extensive uptake and activation of hydrophobic triphenylphosphonium cations within cells. Biochem. J. (2008) 411, 633-645. (Year: 2008).*

Yova et al., Development of a Fluorescence-Based Imaging System for Colon Cancer Diagnosis Using Two Novel Rhodamine Derivatives. Lasers Med Sci 2000, 15:140-147. (Year: 2000).*

International Patent Application No. PCT/US2015/043398, filed Aug. 3, 2015; International Search Report and Written Opinion dated Nov. 9, 2015; 8 pages.

International Patent Application No. PCT/US2015/043398, filed Aug. 3, 2015; International Preliminary Report on Patentability dated Feb. 16, 2017; 4 pages.

Abbott, "Astrocyte-endothelial interactions and blood-brain barrier permeability" *J Anat*, Jun. 2002; 200(6):629-38.

Bolon et al., "STP position paper: Recommended practices for sampling and processing the nervous system (brain, spinal cord, nerve, and eye) during nonclinical general toxicity studies" Toxicol Pathol, 2013; 41(7):1028-48. Epub Mar. 7, 2013.

Bowman et al., "Trends in hospitalizations associated with pediatric traumatic brain injuries" *Pediatrics*, Nov. 2008; 122(5):988-93.

Chodobski et al., "Blood-brain barrier pathophysiology in traumatic brain injury" *Translational Stroke Research*, Dec. 2011; 2(4):492-516.

Coronado et al. "Surveillance for traumatic brain injury-related deaths—United States, 1997-2007." MMWR Surveill Summ, May 6, 2011; 60(5):1-32.

Dalla Libera et al. "IL-6 polymorphism associated with fatal outcome in patients with severe traumatic brain injury" Brain Inj, 2011; 25(4):365-69. Epub Feb. 11, 2011.

Daniel et al., "Intracellular distribution of psychotropic drugs in the grey and white matter of the brain: the role of lysosomal trapping" J Pharmacol, Oct. 2001; 134(4):807-14.

Dos Santos et al., "Control of lymphocyte adhesion to brain and aortic endothelium: ICAM-1, VCAM-1 and negative charge" J Neuroimmunol, May 1996; 66(1-2):125-34.

Du et al., "Dynamic regulation of mitochondrial function by glucocorticoids" Proc Natl Acad Sci USA, Mar. 3, 2009; 106(9):3543-8. Epub Feb. 6, 2009.

Duberstein et al., "Gait analysis in a pre- and post-ischemic stroke biomedical pig model" Physiol. Behav., Feb. 10, 2014; 125:8-16. Epub Nov. 25, 2013.

Duhaime et al., "Magnetic resonance imaging studies of age-dependent responses to scaled focal brain injury in the piglet" J Neurosurg, Sep. 2003; 99:542-8.

Frugier et al., "In situ detection of inflammatory mediators in post mortem human brain tissue after traumatic injury" J Neurotrauma, Mar. 2010; 27(3):497-507.

Guadagno et al., "Microglia-derived TNFalpha induces apoptosis in neural precursor cells via transcriptional activation of the Bcl-2 family member Puma" Cell Death Dis, Mar. 14, 2013; 4:e538.

Herve et al., "CNS delivery via adsorptive transcytosis" AAPS J, Sep. 2008; 10(3):455-72. Epub Aug. 26, 2008.

Kalayci et al., "Effect of Coenzyme $Q_{10}$ on ischemia and neuronal damage in an experimental traumatic brain-injury model in rats" BMC Neurosci, Jul. 29, 2011; 12:75. 7 pages.

Kinnunen et al., "White matter damage and cognitive impairment after traumatic brain injury" Brain, Feb. 2011; 134(Pt 2):449-63. Epub Dec. 29, 2010.

Knoblach et al., "Interleukin-10 improves outcome and alters proinflammatory cytokine expression after experimental traumatic brain injury" Exp Neurol, Sep. 1998; 153(1):143-51.

Kossmann et al., "Intrathecal and serum interleukin-6 and the acute-phase response in patients with severe traumatic brain injuries" Shock, Nov. 1995; 4(5):311-7.

Kuluz et al., "New pediatric model of ischemic stroke in infant piglets by photothrombosis: acute changes in cerebral blood flow, microvasculature, and early histopathology" Stroke, Jun. 2007; 38(6):1932-7.

Kumar et al., "Neuroinflammation after traumatic brain injury: opportunities for therapeutic intervention" Brain Behav Immun, Nov. 2012; 26(8):1191-201. Epub Jun. 21, 2012.

Lee et al., "Anti-inflammatory and neuroprotective effects of triptolide on traumatic brain injury in rats" Respir Physiol Neurobiol, Jun. 15, 2012; 182(1):1-8. Epub Feb. 17, 2002.

Lind et al., "The use of pigs in neuroscience: modeling brain disorders" Neurosci Biobehav Rev, 2007; 31(5):728-51. Epub Mar. 4, 2007.

Loane et al., "Neuroprotection for traumatic brain injury: translational challenges and emerging therapeutic strategies" Trends Pharmacol Sci., Dec. 2010; 31(12):596-604. Epub Oct. 29, 2010.

Ma et al., "Transplantation of neural stem cells enhances expression of synaptic protein and promotes functional recovery in a rat model of traumatic brain injury" Mol Med Rep, Sep.-Oct. 2011; 4(5):849-56. Epub Jun. 16, 2011.

Maas et al. "Clinical trials in traumatic brain injury: past experience and current developments" Neurotherapeutics, Jan. 2010; 7(1):115-26.

Marrache et al., "Engineering of blended nanoparticle platform for delivery of mitochondria-acting therapeutics" 2012. Proc Natl. Acad Sci USA, 109(40):16288-16293.

Marrache et al., "Ex vivo programming of dendritic cells by mitochondria-targeted nanoparticles to produce interferon-gamma for cancer immunotherapy" ACS Nano, Aug. 27, 2013; 7(8):7392-402. Epub Aug. 6, 2013.

Marrache et al., "Immune stimulating photoactive hybrid nanoparticles for metastatic breast cancer" Integr Biol (Camb), Jan. 2013; 5(1):215-23.

Marrache et al., "Detouring of cisplatin to access mitochondrial genome for overcoming resistance" Proc Natl Acad Sci USA, Jul. 22, 2014; 111(29):10444-9. Epub Jul. 7, 2014.

McConeghy et al., "A review of neuroprotection pharmacology and therapies in patients with acute traumatic brain injury" CNS Drugs, Jul. 1, 2012; 26(7):613-36.

McManus et al., "The Mitochondria-Targeted Antioxidant MitoQ Prevents Loss of Spatial memory Retention and Early Neuropathology in a Transgenic Mouse Model of Alzheimer's Disease" J Neuroscience, Nov. 2, 2011; 31(44):15703-15.

Missios et al., "Scaled cortical impact in immature swine: effect of age and gender on lesion volume" J Neurotrauma, Nov. 2009; 26(11):1943-51.

Narayan et al., "Clinical trials in head injury" J Neurotrauma, May 2002; 19(5):503-57.

Oldendorf et al., "The large apparent work capability of the blood-brain barrier: a study of the mitochondrial content of capillary endothelial cells in brain and other tissues of the rat" Ann Neurol, May 1977; 1(5)409-17.

(56) References Cited

OTHER PUBLICATIONS

Perez-Pinzon et al., "CGS 19755 (Selfotel): A Novel Neuroprotective Agent Against CNS Injury" CNS Drug Rev, Sep. 1, 1996; 2(3):257-68.
Platt et al., "Development and characterization of a Yucatan miniature biomedical pig permanent middle cerebral artery occlusion stroke model" Exp Transl Stroke Med, Mar. 23, 2014; 6(1):5.
Porteous et al., "P-glycoprotein (Mdr1a/1b) and breast cancer resistance protein (Bcrp) decrease the uptake of hydrophobic alkyl triphenylphosphonium cations by the brain" Biochim Biophys Acta, Jun. 2013; 1830(6):3458-65. Epub Feb. 21, 2013.
Quinzii et al., "Coenzyme Q and mitochondrial disease" Developmental disabilities research reviews, Jun. 2010; 16(2):183-8.
Ransohoff et al., "Innate immunity in the central nervous system" J Clin Invest, Apr. 2, 2012; 122(4):1164-71.
Raslan et al., "Medical management of cerebral edema" Neurosurg Focus, May 15, 2007; 22(5):E12.
Salvador-Morales et al., "Immunocompatibility properties of lipid-polymer hybrid nanoparticles with heterogeneous surface functional groups" Biomaterials, 2009; 30:2231-40.
Sharma et al., "Design and Evaluation of multifunctional nanocarriers for selective delivery of coenzyme Q10 to Mitochondria" Biomacromolecules, Jan. 9, 2012; 13(1):239-52. Published online Dec. 16, 2011.
Shear et al., "Neural progenitor cell transplants promote long-term functional recovery after traumatic brain injury" Brain Res, Nov. 5, 2004; 1026(1):11-22.
Sullivan et al., "Behavioral deficits and axonal injury persistence after rotational head injury are direction dependent" J Neurotrauma, Apr. 1, 2013; 30(7):538-45.
Summers et al., *Veterinary Neuropathology*, Mosby: St. Louis, MO; 1994. Cover page, title page and table of contents.
Tanaka et al., "Experimental model of lacunar infarction in the gyrencephalic brain of the miniature pig: neurological assessment and histological, immunohistochemical, and physiological evaluation of dynamic corticospinal tract deformation" Stroke, Jan. 2008; 39(1):205-12. Epub Nov. 29, 2007.
Wallenquist et al., "Grafted neural progenitors migrate and form neurons after experimental traumatic brain injury" Restor Neurol Neurosci, 2009; 27(4):323-34.
Watanabe et al., "MR-based statistical atlas of the Göttingen minipig brain" NeuroImage, Nov. 2001; 14(5):1089-96.
Werner and Engelhard, "Pathophysiology of traumatic brain injury" Br J Anaesth, Jul. 2007; 99(1):4-9.
Wolburg et al., "Brain endothelial cells and the glio-vascular complex" Cell Tissue Res, Jan. 2009; 335(1):75-96.
Woodcock et al., "The role of markers of inflammation in traumatic brain injury" Front Neurol, Mar. 4, 2013; 4:18.
Xiong et al., "Increased brain injury and worsened neurological outcome in interleukin-4 knockout mice after transient focal cerebral ischemia" Stroke, Jul. 2011; 42(7):2026-32. Epub May 19, 2011.
Yakovlev and Faden, "Caspase-dependent apoptotic pathways in CNS injury" Mol Neurobiol, Aug.-Dec. 2001; 24(1-3):131-44.
Yan et al., "Post-traumatic hypoxia exacerbates neurological deficit, neuroinflammation and cerebral metabolism in rats with diffuse traumatic brain injury" J Neuroinflammation, Oct. 28, 2011; 8:147.
Zhang et al., "A universal scaling law between gray matter and white matter of cerebral cortex" Proc Natl Acad Sci USA, May 9, 2000; 97(10):5621-6.
Ziebell et al., "Involvement of pro- and anti-inflammatory cytokines and chemokines in the pathophysiology of traumatic brain injury" Neurotherapeutics, Jan. 2010; 7(1):22-30.
Chang et al., "A Phase I Trial of Tumor Lysate-pulsed Dendritic Cells in the Treatment of Advanced Cancer" Clin Can Res, Apr. 2002; 8:1021-32.
Gollnick et al., "Generation of Effective Antitumor Vaccines Using Photodynamic Therapy" Can Res, Mar. 15, 2002; 62:1604-8.
Igarashi et al., "Liposomal photofrin enhances therapeutic efficacy of photodynamic therapy against the human gastric cancer" Toxicology Letters, 2003; 145:133-41.
Sadzuka et al., "The phototoxicity of photofrin was enhanced by PEGylated liposome in vitro" Cancer Letters, 2006; 241:42-8.
International Patent Application No. PCT/US2015/020591, filed Mar. 12, 2015; International Search Report and Written Opinion dated Jun. 10, 2015; 9 pages.
International Patent Application No. PCT/US2015/020591, filed Mar. 12, 2015; International Preliminary Report on Patentability dated Sep. 22, 2016; 6 pages.
Arvizo et al., "Gold Nanoparticles: Opportunities and Challenges in Nanomedicine" Expert Opin. Drug Deliv., 2010; 7:753-63.
Arvizo et al., "Inhibition of Tumor Growth and Metastasis by a Self-Therapeutic Nanoparticle" Proc. Natl. Acad. Sci. USA, 2013; 110:6700-5.
Birsoy et al., "MCT1-Mediated Transport of a Toxic Molecule Is an Effective Strategy for Targeting Glycolytic Tumors" Nat. Genet., 2013; 45:104-8.
Bustamante et al., "High Aerobic Glycolysis of Rat Hepatoma Cells in Culture: Role of Mitochondrial Hexokinase" Proc. Natl. Acad. Sci. USA, 1977; 74:3735-9.
Chen, "Mitochondrial Membrane Potential in Living Cells" Annu. Rev. Cell. Biol., 1988; 4:155-81.
Chen et al, "Role of Mitochondria-Associated Hexokinase II in Cancer Cell Death Induced by 3-Bromopyruvate" Biochim. Biophys. Acta, 2009; 178:553-60.
Dell'Antone, P., "Targets of 3-Bromopyruvate, a New, Energy Depleting, Anticancer Agent" Med. Chem., Nov. 2009; 5(6):491-6.
Dhar et al., "Polyvalent Oligonucleotide Gold Nanoparticle Conjugates as Delivery Vehicles for Platinum(IV) Warheads" J. Am. Chem. Soc., 2009; 131:14652-3.
Dhar et al., "Targeted delivery of a cisplatin prodrug for safer and more effective prostate cancer therapy in vivo" Proc Natl Acad Sci USA, 2011; 108(5):1850-5.
Giljohann et al., "Gold Nanoparticles for Biology and Medicine" Angew. Chem. Int. Ed., 2010; 49:3280-94.
Higgins et al., "Hypoxia and the Metabolic Phenotype of Prostate Cancer Cells" Biochim. Biophys. Acta, 2009; 1787:1433-43.
Hrkach et al., "Preclinical Development and Clinical Translation of a PSMA-Targeted Docetaxel Nanoparticle with a Differentiated Pharmacological Profile" Sci. Transl. Med., Apr. 4, 2012; 4(128):128ra39.
Hsu et al., "Cancer Cell Metabolism: Warburg and Beyond" Cell, 2008; 134:703-7.
Kingshott et al., "Surfaces That Resist Bioadhesion" Curr. Opin. Solid State Mater. Sci., Aug. 31, 1999; 4(4):403-12.
Marrache et al., "The 'Energy Blocker' inside the 'Power House': Mitochondria targeted delivery of 3-bromopyruvate" Manuscript. ACS Nano, 2014; 38 pages.
Marrache et al., "The Energy Blocker inside the Power House: Mitochondria targeted delivery of 3-bromopyruvate" Supporting Information. Chem Sci, 2014; 14 pages.
Marrache et al., "The energy blocker inside the power house: Mitochondria targeted delivery of 3-bromopyruvate" Chem. Sci, Mar. 2015; 6(3):1832-45.
Mathupala et al., "Hexokinase II: Cancer's Double-Edged Sword Acting as Both Facilitator and Gatekeeper of Malignancy When Bound to Mitochondria" Oncogene, 2006; 25:4777-86.
Modica-Napolitano et al., "Delocalized Lipophilic Cations Selectively Target the Mitochondria of Carcinoma Cells" Adv. Drug Deliv. Rev., Jul. 2001; 49(1-2):63-70.
Nakashima et al., "Purification and Characterization of a Bindable Form of Mitochondrial Bound Hexokinase from the Highly Glycolytic AS-30D Rat Hepatoma Cell Line" Cancer Res., 1988; 48(4):913-9.
Pan et al., "Gold Nanoparticles of Diameter 1.4 Nm Trigger Necrosis by Oxidative Stress and Mitochondrial Damage" Small, Sep. 2009; 5(18):2067-76.
Pastorino et al., "Mitochondrial Binding of Hexokinase II Inhibits Bax-Induced Cytochrome C Release and Apoptosis" J. Biol. Chem., 2002; 277:7610-8.

(56) References Cited

OTHER PUBLICATIONS

Pedersen et al., "Mitochondrial Bound Type II Hexokinase: A Key Player in the Growth and Survival of Many Cancers and an Ideal Prospect for Therapeutic Intervention" Biochim. Biophys. Acta, 2002; 1555:14-20.
Pedersen, "3-Bromopyruvate (3BP) a Fast Acting, Promising, Powerful, Specific, and Effective "Small Molecule" Anti-Cancer Agent Taken from Labside to Bedside: Introduction to a Special Issue" J. Bioenerg. Biomembr., Feb. 2012; 44(1):1-6.
Porporato et al., "Anticancer Targets in the Glycolytic Metabolism of Tumors: A Comprehensive Review" Front. Pharmacol., 2011; 2:49.
Rosi et al., "Oligonucleotide-Modified Gold Nanoparticles for Intracellular Gene Regulation" Science, May 19, 2006; 312(5776):1027-30.
Ross et al., "Lipophilic Triphenylphosphonium Cations as Tools in Mitochondrial Bioenergetics and Free Radical Biology" Biochemistry (Mosc), 2005; 70:222-30.
Seferos et al. "Polyvalent DNA Nanoparticle Conjugates Stabilize Nucleic Acids" Nano Lett., 2009; 9:308-11.
Vander Heiden et al., "Understanding the Warburg Effect: The Metabolic Requirements of Cell Proliferation" Science, 2009; 324:1029-33.
Wang et al., "Photothermal Effects of Supramolecularly Assembled Gold Nanoparticles for the Targeted Treatment of Cancer Cells" Angew. Chem. Int. Ed., 2010; 49:3777-81.
Warburg, "On the Origin of Cancer Cells" Science, Feb. 24, 1956; 123(3191):309-14.
Wilson, "Isozymes of Mammalian Hexokinase: Structure, Subcellular Localization and Metabolic Function" J. Exp. Biol., 2003; 206:2049-57.
International Patent Application No. PCT/US2014/033431, filed Apr. 9, 2014; International Search Report and Written Opinion dated Oct. 27, 2014; 15 pages.
International Patent Application No. PCT/US2014/033431, filed Apr. 9, 2014; International Preliminary Report on Patentability dated Oct. 22, 2015; 11 pages.
International Patent Application No. PCT/US2014/015744, filed Feb. 11, 2014; International Search Report and Written Opinion dated May 26, 2014; 15 pages.
International Patent Application No. PCT/US2014/015744, filed Feb. 11, 2014; International Preliminary Report on Patentability dated Aug. 20, 2015; 10 pages.
International Preliminary Report on Patentability for PCT/US2012/053307, dated Mar. 4, 2014. 2 pages total.
International Search Report/Written Opinion for PCT/US2012/053307, dated Jan. 18, 2013. 10 pages total.
International Patent Application No. PCT/US2013/026299, filed Feb. 15, 2013; International Search Report / Written Opinion dated Apr. 12, 2013; 9 pages.
International Patent Application No. PCT/US2013/026299, filed Feb. 15, 2013; International Preliminary Report on Patentability dated Aug. 28, 2014; 2 pages.
Extended European Search Report for EP 12 82 9002, derived from PCT/US2012/053307, dated May 22, 2015; 8 pages.
European Patent Application No. 13 74 9000.9, filed Sep. 5, 2014; Extended EP Search Report and Search Opinion dated Sep. 21, 2015; 13 pages.
European Patent Application No. 14 78 2682, filed Oct. 26, 2015; Supplementary European Search Report dated Sep. 2, 2016; 5 pages.
Agemy et al. "Targeted nanoparticle enhanced proapoptotic peptide as potential therapy for glioblastoma" 2011. Proc Natl Acad Sci USA. 108(42):17450-17455.
Aggarwal et al., "A dimeric Peptide that Binds Selectively to Prostate-Specific Membrane Antigen and Inhibits its Enzymatic Activity" Cancer Research, Sep. 2006; 23 pages.
Alexis et al. (2008) Factors affecting the clearance and biodistribution of polymeric nanoparticles. *Mol Pharm* 5(4):505-515.
Alexis F, et al. (2008) HER-2-Targeted Nanoparticle-Affibody Bioconjugates for Cancer Therapy. *ChemMedChem.*

Ammirante M, Luo JL, Grivennikov S, Nedospasov S, & Karin M (2010) B-cell-derived lymphotoxin promotes castration-resistant prostate cancer. Nature 464(7286):302-305.
Attard G, Richards J, & de Bono JS (2011) New strategies in metastatic prostate cancer: Targeting the androgen receptor signaling pathway. Clin. Cancer Res. 17(7):1649-1657.
Baas et al., "Slipping Therapeutics to the Mitochondria" SciBX 5(38), Published online Sep. 27, 2012. 4 pages.
Bagalkot V, et al. (2007) Quantum dot-aptamer conjugates for synchronous cancer imaging, therapy, and sensing of drug delivery based on bi-fluorescence resonance energy transfer. *Nano Lett* 7(10):3065-3070.
Baker GL, Jiang X, Vogel EB, & Smith MR (2008) "Clickable" polyglycolides: Tunable synthons for thermoresponsive, degradable polymers. *Macromolecules* 41(6):1937-1944.
Beltran et al., "New therapies for castration-resistant prostate cancer: Efficacy and safety" Eur Urol, Aug. 2011; 60(2):279-90. Epub May 4, 2011.
Bertram JP, et al. (2009) Functionalized poly(lactic-co-glycolic acid) enhances drug delivery and provides chemical moieties for surface engineering while preserving biocompatibility. *Acta Biomater*, 5(8):2860-2871.
Biswas et al., "Liposomes loaded with paclitaxel and modified with novel triphenylphosphonium-PEG-PE conjugate possess low toxicity, target mitochondria and demonstrate enhanced antitumor effects in vitro and in vivo" J. Control. Rel., online Jan. 20, 2012, 159: 393-402.
Braillon, "Re: Himisha Beltran, Tomasz M. Beer, Michael A. Carducci, et al. New therapies for castration-resistant prostate cancer: efficacy and safety. Eur urol 2011; 60:279-90" Eur Urol. Oct. 2011; 60(4):e33. Epub Jul. 13, 2011.
Brigger I, et al. (2004) Negative preclinical results with stealth nanospheres-encapsulated Doxorubicin in an orthotopic murine brain tumor model. *J Control Release* 100(1):29-40.
Butera et al. "Peptidic targeting of phosphatidylserine for the MRI detection of apoptosis in atherosclerotic plaques". 2009. *Mol. Pharm.* 6:1903-1919.
Chalmers et al. "Selective uncoupling of individual mitochondria within a cell using a mitochondria-targeted photoactivated protonophore" 2012. *J. Am Chem Soc.* 134(2):758-761.
Chan JM, et al. (2009) PLGA-lecithin-PEG core-shell nanoparticles for controlled drug delivery. *Biomaterials* 30(8):1627-1634.
Chang SS, et al. (1999) Prostate-specific membrane antigen is produced in tumor-associated neovasculature. *Clin Cancer Res* 5(10):2674-2681.
Cheng J, et al. (2007) Formulation of functionalized PLGA-PEG nanoparticles for in vivo targeted drug delivery. *Biomaterials* 28(5):869-876.
Chou et al., "Photodynamic Therapy: Applications in Atherosclerotic Vascular Disease with Motexafin Lutetium" Catheterization and Cardiovascular Interventions, 2002; 57:387-94.
Clementi et al., "Dendritic Poly(ethylene glycol) Bearing Paclitaxel and Alendronate for Targeting Bone Neoplasms" Molecular Pharmaceutics, May 24, 2011; 8:1063-72.
Dhar et al. (2008) Targeted delivery of cisplatin to prostate cancer cells by aptamer functionalized Pt(IV) prodrug-PLGA-PEG nanoparticles. *Proc Nad Acad Sci USA* 105(45):17356-17361.
Dhar et al. (2011) Targeted delivery of a cisplatin prodrug for safer and more effective prostate cancer therapy in vivo. *Proc Natl Acad Sci USA* 108(5):1850-1855.
De Gaetano Donati et al., "HIV infection, HAART, and endothelial adhesion molecules: current perspectives" Lancet Infect Dis, Apr. 2004; 4(4):213-222.
De Marzo et al., "Inflammation in prostate carcinogenesis" Nat Rev Cancer, Apr. 2007; 7(4):256-269.
Farokhzad OC, et al. (2004) Nanopartide-aptamer bioconjugates: A new approach for targeting prostate cancer cells. *Cancer Res* 64(21):7668-7672.
Farokhzad OC, et al. (2006) Targeted nanoparticle-aptamer bioconjugates for cancer chemotherapy in vivo. *P Natl Acad Sci USA* 103(16):6315-6320.

(56) References Cited

OTHER PUBLICATIONS

Ferlay et al., "Estimates of cancer incidence and mortality in Europe in 2008" Eur J Cancer, Mar. 2010; 46(4):765-781. Epub Jan. 29, 2010.

Fricke et al., "Mycobacteria Induce IFN-g Production in Human Dendritic Cells via Triggering of TLR2" J Immunol, 176-5173-82.

Fujimoto et al., "Novel therapeutic strategies following docetaxel-based chemotherapy in castration-resistant prostate cancer" Expert Rev Clin Pharmacol, Nov. 2010; 3(6):785-795.

Fulda et al. "Targeting Mitochondria for cancer therapy". 2010. *Nature Reviews—Drug Discovery.* 9:447.

Galsky et al. (2010) Cabazitaxel. *Nat Rev Drug Discov* 9(9):677-678.

Galsky MD & Vogelzang NJ (2010) Docetaxel-based combination therapy for castration-resistant prostate cancer. *Ann Oncol* 21(11):2135-2144.

Gerhardt WW, et al. (2006) Functional lactide monomers: methodology and polymerization. *Biomacromolecules* 7(6):1735-1742.

Ghosh A & Heston WD (2004) Tumor target prostate specific membrane antigen (PSMA) and its regulation in prostate cancer. *J Cell Biochem* 91(3):528-539.

Gomes et al. "Characterization of PLGA microparticles as a drug carrier for 3-ethoxycarbony1-2h-benzofuro[3,2-f]-1-benzopyran-2-one. Ultrastructural study of cellular uptake and intracellular distribution" 2006. *Drug Deliv.* 13(6):447-454.

Gosh et al. "Nanocapsulated curcumin: oral chemopreventive formulation against diethylnitrosamine induced hepatocellular carcinoma in rat". 2012. *Chem. Biol. Interact.* 195(3):206-214.

Gratton SE, et al. (2008) The effect of particle design on cellular internalization pathways. *Proc Nall Acad Sci USA* 105(33):11613-11618.

Gref R, et al. (1994) Biodegradable long-circulating polymeric nanospheres. *Science* 263(5153):1600-1603.

Gu F, et al. (2008) Precise engineering of targeted nanoparticles by using self-assembled biointegrated block copolymers. *Proc Natl Acad Sci U S A* 105(7):2586-2591.

Higuchi et al., "Mannosylated semiconductor quantum dots for the labeling of macrophages" J Control Release, Jan. 22, 2008; 125(2):131-6. Available Online Oct. 17, 2007.

Hoye et al. "Targeting mitochondria". 2008. *ACC Chem Res.* 41(1):87-97.

Hussain S, Pluckthun A, Allen TM, & Zangemeister-Wittke U (2007) Antitumor activity of an epithelial cell adhesion molecule targeted nanovesicular drug delivery system. *Mol Cancer Ther* 6(11):3019-3027.

Jain RK (2001) Delivery of molecular and cellular medicine to solid tumors. *Adv Drug Deliv Rev* 46(1-3):149-168.

Jain JP, Yenet Ayen W, Domb AJ, & Kumar N (2011) Biodegradable Polymers in Drug Delivery. *Biodegradable Polymers in Clinical Use and Clinical Development,* (John Wiley & Sons, Inc.), pp. 1-58.

Jemal et al., "Cancer statistics, 2010" CA Cancer J Clin, Sep.-Oct. 2010; 60(5):277- 300. Epub Jul. 7, 2010.

Jia et al. (2009) Mechanisms of drug combinations: interaction and network perspectives. *Nat Rev Drug Discov* 8(2):111-128.

Jing F & Hillmyer MA (2008) A bifunctional monomer derived from lactide for toughening polylactide. *J Am Chem Soc* 130(42):13826-13827.

Karakunnel J & Dahut W (2008) Castrate-resistant prostate cancer: the right targets and combinations. *Therapy* 5(1):57-61.

Khor et al. (2007) COX-2 expression predicts prostate-cancer outcome: analysis of data from the RTOG 92-02 trial. *Lancet Oncol* 8(10):912-920.

Kirpotin DB, et al. (2006) Antibody targeting of long-circulating lipidic nanoparticles does not increase tumor localization but does increase internalization in animal models. *Cancer Res* 66(13):6732-6740.

Kolishetti et al., "Engineering of self-assembled nanoparticle platform for precisely controlled combination drug therapy" Proc Natl Acad Sci USA, 2010; 107(42):17939-17944.

Kong G, Braun RD, & Dewhirst MW (2000) Hyperthermia enables tumor-specific nanoparticle delivery: effect of particle size. *Cancer Res* 60(16):4440-4445.

Langer R (2001) Drug delivery. Drugs on target. *Science* 293(5527):58-59.

Laurent BA & Grayson SM (2011) Synthesis of Cyclic Dendronized Polymers via Divergent "Graftfrom" and Convergent Click "Graft-to" Routes: Preparation of Modular Toroidal Macromolecules. *J Am Chem Soc.*

Li X, Guo J, Asong J, Wolfert MA, & Boons GJ (2011) Multifunctional surface modification of goldstabilized nanoparticles by bioorthogonal reactions. *J Am Chem Soc* 133(29):11147-11153.

Liu et al., "Interactions of serum proteins with small unilamellar liposomes composed of dioleoylphosphatidylethanolamine and oleic acid: high-density lipoprotein, apolipoprotein A1, and amphipathic peptides stabilize liposomes" Biochemistry, Apr. 17, 1990; 29(15):3637-43.

Madu et al., "Review: Novel diagnostic biomarkers for prostate cancer" J Cancer 1:150-177.

Mamo et al., "Emerging nanotechnology approaches for HIV/AIDS treatment and prevention" Nanomedicine, 2010; 5(2):269-285.

Marrache et al., "Functionalized Polymers for Mitochondria Trafficking of Nanoparticles" Methods Mol Biol, 2012; 1265:103-12.

Marrache et al., "Immune stimulating photoactive hybrid nanoparticles for metastatic breast cancer" Integr Biol, 2013; 5:215-23.

Marrache et al., "Ex vivo generation of functional immune cells by mitochondria-targeted photosensitization of cancer cells" Methods Mol Biol, 2015; 1265:113-22.

Matsumura Y & Maeda H (1986) A new concept for macromolecular therapeutics in cancer chemotherapy: mechanism of tumoritropic accumulation of proteins and the antitumor agent smancs. *Cancer Res* 46(12 Pt 1):6387-6392.

Melo et al. "Nanocytotoxicity: violacein and violacein-loaded poly (D, L-lactide-co-glycolide) nanoparticles acting on human leukemic cells". 2009. *J. Biomed Nanotechnol.* 5(2).192-201.

Milowsky MI, et al. (2007) Vascular targeted therapy with anti-prostate-specific membrane antigen monoclonal antibody J591 in advanced solid tumors. *J Clin Oncol* 25(5):540-547.

Morgan et al., "Mitochondria-based photodynamic anti-cancer therapy" Advanced Drug Deliv Rev, 2001; 49:71-86.

Morris MJ, et al. (2007) Phase I evaluation of J591 as a vascular targeting agent in progressive solid tumors. *Clin Cancer Res* 13(9):2707-2713.

Murphy et al. "Targeting antioxidants to mitochondria by conjugation to lipophilic cations". 2007. *Annu Rev Pharmacol Toxicol.* 47:629-656.

Norrish et al., "Non-Steroidal anti-inflammatory drugs and prostate cancer progression" Int J Cancer, 1998; 77:511-5.

Oda et al., "Preparation of a water-soluble fluorinated zinc phthalocyanine and its effect for photodynamic therapy" J Photochem Photobiol B: Biology, 2000; 59:20-5.

Owens DE & Peppas NA (2006) Opsonization, biodistribution, and pharmacokinetics of polymeric nanoparticles. *Int J Pharmaceut* 307(1):93-102.

Park et al., "A new atherosclerotic lesion probe based on hydrophobically modified chitosan nanoparticles functionalized by the atherosclerotic plaque targeted peptides" J Control Release, Jun. 24, 2008; 128(3):217-23. Available Online Mar. 28, 2008.

Pathak et al., "The Prodrug platin-A: simultaneous release of cisplatin and aspirin" Agnew Chem Int Ed Engl, Feb. 10, 2014; 53(7):1963-7.

Petrylak DP, et al. (2004) Docetaxel and estramustine compared with mitoxantrone and prednisone for advanced refractory prostate cancer. *N Engl J Med* 351(15):1513-1520.

Pirollo KF & Chang EH (2008) Does a targeting ligand influence nanoparticle tumor localization or uptake? *Trends Biotech* 26(10):552-558.

Porteous et al. "Rapid uptake of lipophilic triphenylphosphonium cations by mitochondria in vivo following intravenous injection: implications for mitochondria-specific therapies and probes", 2010. *Biochim Biophys Acta.* 1800(9):1009-1017.

(56) References Cited

OTHER PUBLICATIONS

Prime et al. "A mitochondria-targeted S-nitrosothiol modulates respiration, nitrosates thiols, and protects against ischemia-reperfusion injury" 2009. *Proc Natl Acad Sci USA*. 106(26):10765-10769.
Pujol et al., (2010) Unveiling the role of network and systems biology in drug discovery. *Trends Pharmacol Sci* 31(3):115-123.
Pun et al. (2004) Targeted delivery of RNA-cleaving DNA enzyme (DNAzyme) to tumor tissue by transferrin-modified, cyclodextrin-based particles. *Cancer Biol Ther* 3(7):641-650.
Shamash J, et al. (2010) A validated prognostic index predicting response to dexamethasone and diethylstilbestrol in castrate-resistant prostate cancer. *Cancer* 116(15):3595-3602.
Smith et al. "Delivery of bioactive molecules to mitochondria in vivo". 2003. *Proc Natl Acad Sci USA*. 100(9):5407-5412.
Smith et al. "Selective targeting of an antioxidant to mitochondria". 1999. *Eur J. Biochem*. 263(3):709-716.
Smith et al., "Pamidronate to Prevent Bone Loss During Androgen-Deprivation Therapy for Prostate Cancer" New Enlg J Med, Sep. 27, 2001; 345(13):948-55.
Soppimath et al. (2001) Biodegradable polymeric nanoparticles as drug delivery devices. *J Controlled Rel* 70(1-2):1-20.
Swamakar et al. "Oral bioavailability, therapeutic efficacy and reactive oxygen species scavenging properties of coenzyme Q10-loaded polymeric nanoparticles". 2011. *Biomaterials*. 32(28):6860-6874.
Taneja SS (2004) ProstaScint(R) Scan: Contemporary Use in Clinical Practice. *Rev Urol* 6 Suppl 10:S19-28.
Tannock et al. (2004) Docetaxel plus prednisone or mitoxantrone plus prednisone for advanced prostate cancer. *N Engl J Med* 351(15):1502-1512.
Uemura H, et al. (2010) Immunological evaluation of personalized peptide vaccination monotherapy in patients with castration-resistant prostate cancer. *Cancer Sci* 101(3):601-608.
Ullen et al., "Additive/synergistic antitumoral effects on prostate cancer cells in vitro following treatment with a combination of docetaxel and zoledronic acid" Acta Oncologica, 2005; 44:644-50.
Verma A, et al. (2008) Surface-structure-regulated cell-membrane penetration by monolayer-protected nanoparticles. *Nature Mat* 7(7):588-595.
Wang et al. "Alpha-tocopheryl polyethylene glycol succinate-emulsified poly(lactic-co-glycolic acid) nanoparticles for reversal of multidrug resistance in vitro". *Nanotechnology*. 2012. 23(49):495103.
Weiss et al., "Coupling of biotin-(poly(ethylene glycol))amine to poly(D,L-lactide-co-glycolide) nanoparticles for versatile surface modification" Bioconjug Chem, Jul.-Aug. 2007; 18(4):1087-94. Published Online Jun. 23, 2007.
Wu P, et al. (2010) Adenovirus targeting to prostate-specific membrane antigen through virus-displayed, semirandom peptide library screening. *Cancer Res* 70(23):9549-9553.
Yuan F, et al. (1994) Microvascular permeability and interstitial penetration of sterically stabilized (stealth) liposomes in a human tumor xenograft. *Cancer Res* 54(13):3352-3356.
Yuan F, et al. (1995) Vascular permeability in a human tumor xenograft: molecular size dependence and cutoff size. *Cancer Res* 55(17):3752-3756.
Zhang L, et al. (2007) Co-delivery of hydrophobic and hydrophilic drugs from nanoparticle-aptamer bioconjugates. *ChemMedChem* 2(9):1268-1271.
Zhang L, et al. (2008) Self-assembled lipid—polymer hybrid nanoparticles: a robust drug delivery platform. *ACS nano* 2(8):1696-1702.
Zhao et al., "Highly Selective Mitochondria-Targeting Amphiphilic Silicone(IV) Phthalocyanines with Axially Ligated Rhodamine B for Photodynamic Therapy" Inorganic Chem, Dec. 22, 2011; 51:812-21.
Aggarwal et al., "A dimeric Peptide that Binds Selectively to Prostate-Specific Membrane Antigen and Inhibits its Enzymatic Activity" Cancer Research, Sep. 15, 2006; 66(18):9171-7.
Alexis et al., "HER-2-Targeted Nanoparticle-Affibody Bioconjugates for Cancer Therapy" ChemMedChem, Dec. 2008; 3(12):1839-43.
Fricke et al., "Mycobacteria Induce IFN-gamma Production in Human Dendritic Cells via Triggering of TLR2" J Immunol, May 1, 2006; 176(9):5173-82.
Madu et al., "Review: Novel diagnostic biomarkers for prostate cancer" J Cancer, Oct. 6, 2010; 1:150-77.
Szeto, "Cell-permeable, mitochondrial-targeted, peptide antioxidants" AAPS J, Jun. 2006; 8(2):E277-E283.
Baas et al., "Slipping Therapeutics to the Mitochondria" SciBX, 5(38). Published Sep. 27, 2012. 4 pages.
Mayo Clinic Staff, Patient Care & Health Information, "Traumatic Brain Injury" [online]. Published by Clinic Staff on or before Jun. 7, 2017. 13 pages.

\* cited by examiner

— T-3-BP-AuNP —

— NT-3-BP-AuNP —

MITOCHONDRIAL DELIVERY OF 3-BROMOPYRUVATE

RELATED APPLICATION

This application is the § 371 U.S. National Stage of International Application No. PCT/US2015/020591, filed Mar. 13, 2015, which claims the benefit of U.S. Provisional Application No. 61/953,159 filed on Mar. 14, 2014, each of which are incorporated herein by reference in their entireties.

FIELD

The present disclosure relates to nanoparticles configured to traffic agents that inhibit hexokinase, such as 3-bromopyruvate, to different compartments of mitochondria such as the outer mitochondrial membrane, the inner mitochondrial membrane, the inter membrane space and methods of use thereof.

INTRODUCTION AND SUMMARY

The majority of cancers use aerobic glycolysis, which is accompanied by high rates of glucose consumption and lactate production, even when oxygen is available for oxidative phosphorylation (OXPHOS). Hexokinase (HK) is a key enzyme involved in the first step of glycolysis pathway in transferring a phosphate group from adenosine triphosphate (ATP) to glucose to produce glucose-6-phosphate. There are four different isoforms HK2-4 in mammalian cells which differ in their expression, subcellular localizations, and catalytic properties. HK 1 and 2 with abilities to bind to mitochondria through their interaction with voltage dependent anion channel (VDAC) play significant roles in the mitochondria homeostasis. The high glycolytic environment of aggressive cancers requires an up-regulation of HK2 protein level in cancer cells. Approximately 80% of HK2 are associated with mitochondria though their interaction with VDAC in cancer cells. Mitochondria-bound HK2 can acquire the required ATP for glucose phosphorylation to accelerate the glycolytic rate and stimulate the tricarboxylic acid (TCA) cycle in the mitochondria. Interactions of VDAC and HK2 on the outer mitochondrial membrane (OMM) not only increase mitochondrial energy metabolism, but also down-regulate the apoptotic pathway by suppressing cytochrome c release. Increased association of HK2 with the mitochondria in cancer cells via VDAC, which has privileged access to mitochondrial ATP and regulates the opening of the mitochondrial permeability transition (MTP) pore causes resistance to apoptosis for cancer cells. This significant translocation of HK2 from cytoplasm to the OMM in cancer cells combined with its important roles in glycolytic pathway makes HK2 an attractive target for anticancer therapeutic modality development. A brominated derivative of pyruvic acid, 3-bromopyruvate (3-BP) is an anti-tumoral alkylating agent that selectively kills cancer cells by inhibiting HK2. 3-BP has the ability to suppress glycolytic capacity of tumor by abolishing the activity of mitochondrially-bound HK2. 3-BP also participates in the inhibition of mitochondrial succinate dehydrogenase, mitochondrial phosphate carrier (PIC), and adenine nucleotide carrier (ANC).

The characteristic alterations of mitochondrial function in cancer, association of HK2 to the OMM via VDAC, the ability of 3-BP in inhibition of HK2, and subsequent apoptosis of cancer cells led to many studies to evaluate the therapeutic potential of 3-BP. However, 3-BP showed limited clinical potential caused by non-specificity such as interaction with HK1 or other metabolic proteins and systemic toxicity. Once inside cells, 3-BP has several nonglycolytic targets, such as V-ATPases, sarcoplasmic reticulum $Ca_{2+}$-ATPases, carbonic anhydrases, and histone deacetylases. A family of proton-coupled monocarboxylate transporters (MCTs) are involved in the transport of monocarboxylic acids such as lactate, pyruvate, butyrate, and acetate across the plasma membrane.

Although these transporters are up-regulated in cancer cells to compensate the increased lactic acid production and consequent efflux by the cell, we hypothesized that 3-BP will face tremendous challenge for its uptake by the MCTs in cancer cells. To circumvent this, mitochondria-targeted local delivery strategies can be extremely important to enhance overall treatment efficacy and to reduce toxic effects of 3-BP.

A variety of targeted-nanoparticles (NPs) have the ability to take the current medicine to the next level by precise delivery, improving pharmacokinetics (PK) and biodistribution (bioD) of small molecule based drugs. One of the most studied nanostructures in medicine is gold NPs (AuNPs) which can be constructed in different sizes, shapes, and have the ability to be decorated with drug molecules and targeting moieties. Furthermore, when AuNPs are illuminated with light of wavelengths of 650-900 nm, the photons will be strongly absorbed or scattered, the absorbed light can be transformed into heat, a process known as the photothermal effect, causing an increase in temperature. The heat generated from the photothermal effect can be used to destroy cancer cells directly.

With these properties in mind, we hypothesized that the use of a mitochondria-targeted AuNP delivery system for 3-BP will allow the delivery of this HK2 inhibitor specifically to mitochondria and subsequent laser irradiation will further enhance the therapeutic efficacy of the engineered construct by photothermal effect. In this disclosure, we highlight the findings related to remarkable increase in anti-tumor activity of 3-BP by mitochondrial delivery using a triphenylphosphonium (TPP) cation modified AuNP (T-3-BPAuNP) (FIG. 1), efficient inhibition of glycolysis, and subsequent changes in the mitochondrial bioenergetics.

In more general terms, nanoparticles, as described in embodiments herein, include a hexokinase-2 inhibitor and a mitochondrial targeting moiety. A gold nanoparticle may include any suitable hexokinase-2 inhibitor. Examples of suitable hexokinase-2 inhibitors include 3-bromopyruvate, 2-deoxy-D-glucose, lonidamine, or the like. The nanoparticles, in embodiments, include a radiation excitable agent that heats on exposure to radiation. Examples of such agents include gold nanoparticles, such as gold nanorods, quantum dots and silver nanoparticles. In embodiments, the nanoparticles comprise carbon nanotubes.

Advantages of one or more of the various embodiments presented herein over prior nanoparticles, imaging methodologies, treatment modalities, or the like will be readily apparent to those of skill in the art based on the following detailed description when read in conjunction with the accompanying drawings.

Figure 1A:
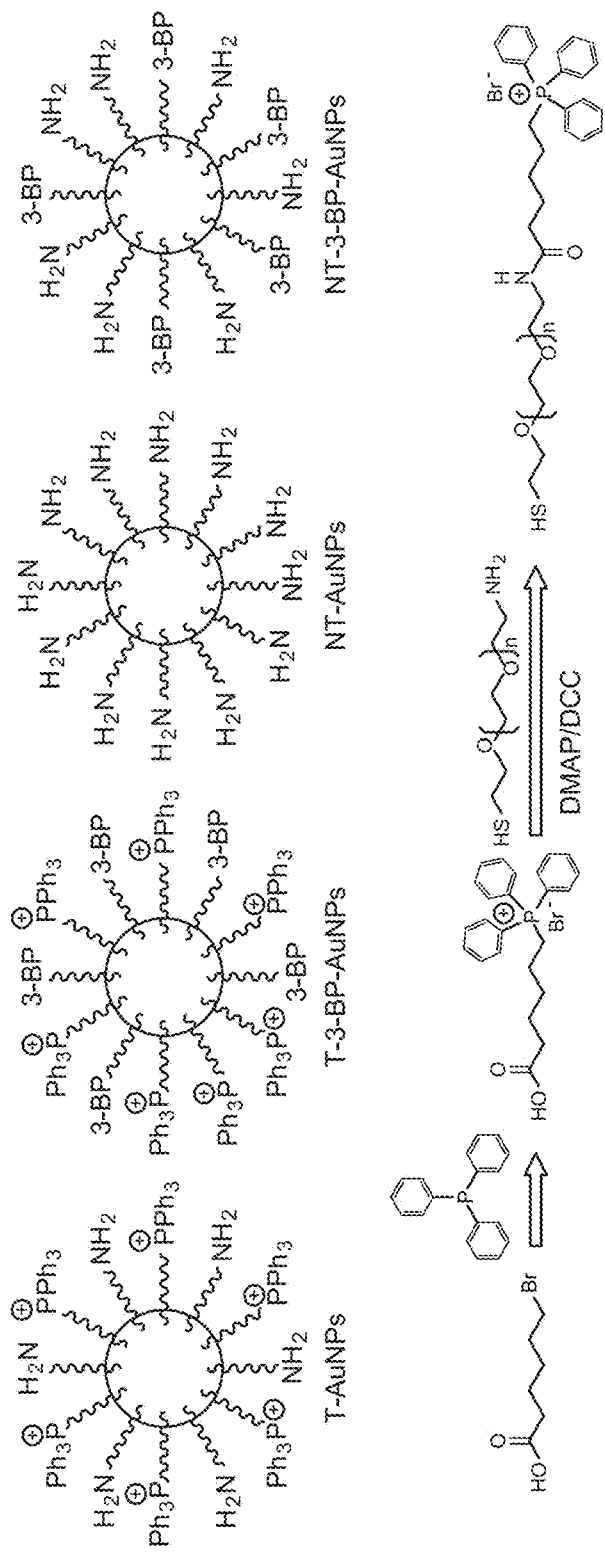
FIGS. 1A-B together are a schematic drawing illustrating engineered AuNP and control NPs used in mitochondria-targeted delivery of 3-BP; including synthesis of mitochondria-targeted TPP-modified PEG ligand, T-AuNP, and conjugation of 3-BP.

The schematic drawings presented herein are not necessarily to scale.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

Nanoparticles, as described in embodiments herein, include a hexokinase-2 inhibitor, a mitochondrial targeting moiety and a radiation excitable agent. In embodiments, the nanoparticles are gold nanoparticles.

The nanoparticles may be formed in any suitable manner. For example, gold nanoparticles may be produced in a liquid by reducing chloroauric acid ($H[AuCl_4]$). After dissolving chloroauric acid, the solution can rapidly stirred while a reducing agent such as $NaBH_4$ is added, causing $Au^{3+}$ ions to be reduced to neutral gold atoms. As more and more of these gold atoms form, the solution becomes supersaturated, and gold gradually starts to precipitate. Agents, such as mitochondrial targeting agents, hexokinase inhibitors and the like may be attached to the gold nanoparticles through an appropriate linker having a reducing group, such as a SH moiety. The agents may be attached to the linkers before or following attachment to the gold particles.

In embodiments, the nanoparticles are silver nanoparticles or carbon nanotubes, which may be synthesized through any suitable technique. Several synthesis schemes for producing silver nanoparticles or carbon nanotubes having bound agents are well known to those of skill in the art. If the nanoparticles are not formed from a radiation excitable core (e.g., if the nanoparticles are not gold nanoparticle, silver nanoparticles, etc.), then a radiation excitable agent may be bond to the core.

The nanoparticles described herein may optionally include a hydrophilic layer surrounding the core (e.g., surrounding a gold nanoparticle core). The hydrophilic layer may assist the nanoparticle in evading recognition by the immune system and may enhance circulation half-life of the nanoparticle.

The hydrophilic layer may be formed, in whole or in part, by a hydrophilic portion of an amphiphilic polymer, such as a block co-polymer having a hydrophobic block and a hydrophilic block; a polysaccharide or the like.

Any suitable hydrophilic polymer or hydrophilic portion of an amphiphilic polymer may form the hydrophilic layer or portion thereof. The hydrophilic polymer or hydrophilic portion of a polymer may be a linear or branched or dendritic polymer. Examples of suitable hydrophilic polymers include polysaccharides, dextran, chitosan, hyaluronic acid, polyethylene glycol (PEG), polymethylene oxide, and the like.

Nanoparticles having a hydrophilic layer may have any suitable diameter. In embodiments, nanoparticles have a diameter of about 250 nm or less; e.g. about 200 nm or less. In embodiments, a nanoparticle effective for mitochondrial targeting has a diameter of about 190 nm or less, about 180 nm or less, about 170 nm or less, about 160 nm or less, about 150 nm or less, about 140 nm or less, about 130 nm or less, about 120 nm or less, about 110 nm or less, about 100 nm or less, about 90 nm or less, about 80 nm or less, about 70 nm or less, about 60 nm or less, about 50 nm or less, about 40 nm or less, about 30 nm or less, about 20 nm or less, or about 10 nm or less. In embodiments, a nanoparticle has a diameter of from about 10 nm to about 250 nm, such as from about 20 nm to about 200 nm, from about 50 nm to about 160 nm, from about 60 nm to about 150 nm, from about 70 nm to about 130 nm, from about 80 nm to about 120 nm, from about 80 nm to about 100 nm, or the like.

The nanoparticles described herein include one or more moieties that target the nanoparticles to mitochondria. As used herein, "targeting" a nanoparticle to mitochondria means that the nanoparticle accumulates in mitochondria relative to other organelles or cytoplasm at a greater concentration than substantially similar non-targeted nanoparticle. A substantially similar non-target nanoparticle includes the same components in substantially the same relative concentration (e.g., within about 5%) as the targeted nanoparticle, but lacks a targeting moiety.

The mitochondrial targeting moieties may be tethered to the core in any suitable manner. In embodiments, a targeting moiety is bound to a gold nanoparticle core via a reduced sulfhydryl moiety of a linker. More than one targeting moiety may be bound to a given nanoparticle.

Examples of targeting moieties tethered to polymers presented throughout this disclosure for purpose of illustrating the types of reactions and tethering that may occur. However, one of skill in the art will understand that tethering of targeting moieties to nanoparticles may be carried out according to any of a number of known chemical reaction processes.

Targeting moieties may be present in the nanoparticles at any suitable concentration. In embodiments, the concentration may readily be varied based on initial in vitro analysis to optimize prior to in vivo study or use. In embodiments, the targeting moieties will have surface coverage of from about 5% to about 100%.

Any suitable moiety for facilitating accumulation of the nanoparticle within the mitochondria may be employed. Due to the substantial negative electrochemical potential maintained across the inner mitochondrial membrane, delocalized lipophilic cations are effective at crossing the hydrophobic membranes and accumulating in the mitochondria. Triphenyl phosophonium (TPP) containing compounds can accumulate greater than 10 fold within the mitochondrial matrix. Any suitable TPP-containing compound may be used as a mitochondrial matrix targeting moiety. Representative examples of TPP-based moieties may have structures indicated below in Formula I, Formula II or Formula III:

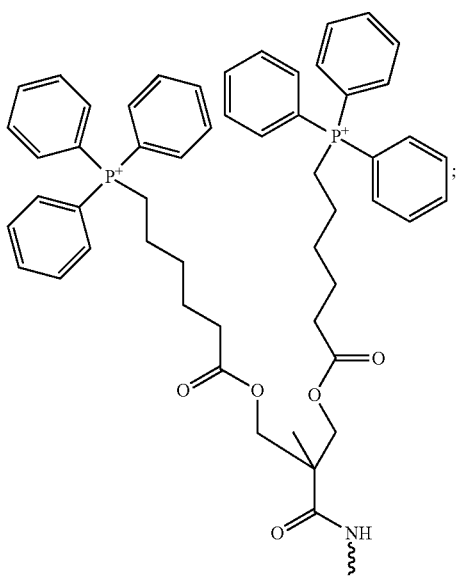

I

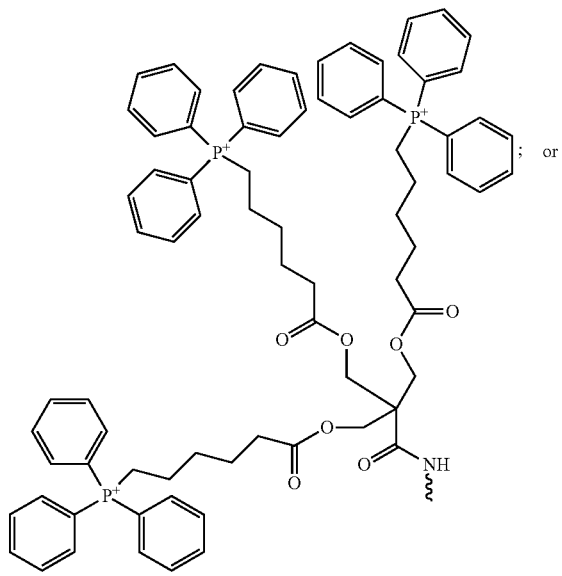

II

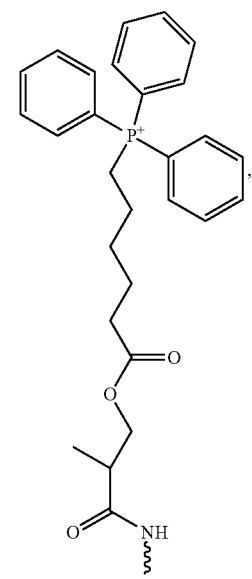

III where the amine (as depicted) may be conjugated to a linker such as a polymer or other component for incorporation into the nanoparticle. Alternatively, the amine may be a sulfhydryl (not shown) or other suitable reducing moiety.

In embodiments, the delocalized lipophilic cation for targeting the mitochondrial matrix is a rhodamine cation, such as Rhodamine 123 having Formula IV as depicted below:

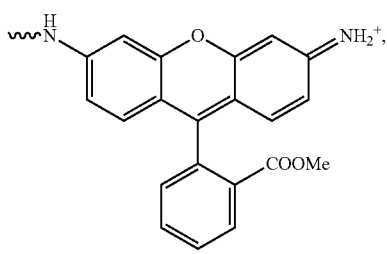

IV where the secondary amine (as depicted) may be conjugated to a linker such as a polymer, lipid, or the like for incorporation into the nanoparticle. Alternatively, the amine may be a sulfhydryl (not shown) or other suitable reducing moiety.

Of course, non-cationic compounds may serve to target and accumulate in the mitochondrial matrix. By way of example, Szeto-Shiller peptide may serve to target and accumulate a nanoparticle in the mitochondrial matrix. Any suitable Szetto-Shiller peptide may be employed as a mitochondrial matrix targeting moiety. Non-limiting examples of suitable Szeto-Shiller peptides include SS-02 and SS-31, having Formula V and Formula VI, respectively, as depicted below:

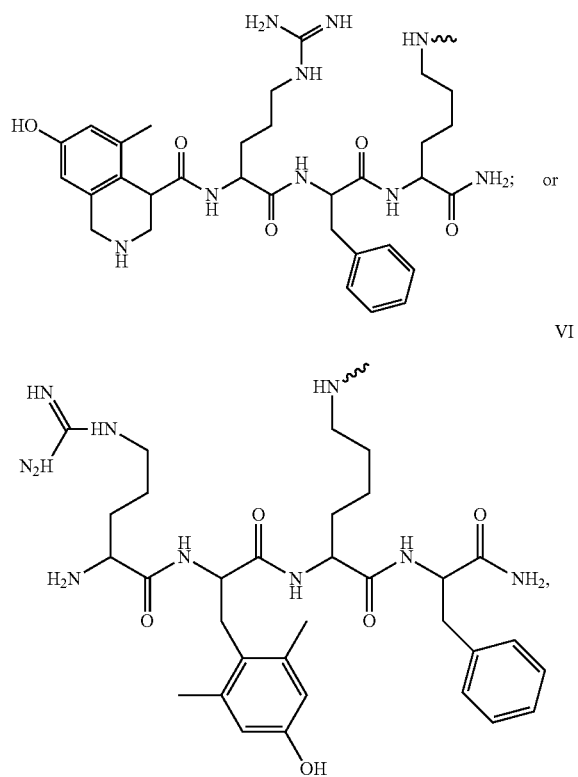

V

VI where the secondary amine (as depicted) may be conjugated to a liker such as a polymer, lipid, or the like for incorporation into the nanoparticle. Alternatively, the amine may be a sulfhydryl (not shown) or other suitable reducing moiety.

A targeting moiety can be attached to a hydrophilic polymer or hydrophilic portion of a polymer so that the targeting moiety will extend from the core of the nanoparticle to facilitate the effect of the targeting moiety.

A nanoparticle, as described herein, may include any one or more hexokinase inhibitors. The hexokinase inhibitor may be a hexokinase-2 inhibitor. Examples of suitable hexokinase inhibitors include 3-bromopyruvate, 2-deoxy-D-glucose, lonidamine, and the like.

The one or more therapeutic agents may be attached to the core of the nanoparticle via a linker and may be released from the core at a desired rate.

In embodiments, a therapeutic agent or precursor thereof is conjugated to a linker attached to the core in a manner similar to that described above with regard to targeting moieties. The therapeutic agent may be conjugated via a cleavable linker so that the agent may be released when the nanoparticle reaches the target location, such as mitochondria.

The therapeutic agents may be present in the nanoparticle at any suitable concentration. For example, a therapeutic agent may be present in the nanoparticle at a concentration from about 0.01% to about 30% by weight of the nanoparticle.

In embodiments, the nanoparticle is useful for treatment of cancer in a subject in need thereof. Any suitable cancer may be treated. In embodiments, the cancer is prostate cancer.

The performance and characteristics of nanoparticles produced herein may be tested or studied in any suitable manner. By way of example, therapeutic efficacy can be evaluated using cell-based assays. Toxicity, bio-distribution, pharmacokinetics, and efficacy studies can be tested in cells or rodents or other mammals. Rodents, rabbits, pigs, or the like may be used to evaluate diagnostic or therapeutic potential of nanoparticles. Some additional details of studies that may be performed to evaluate the performance or characteristics of the nanoparticles, which may be used for purposes of optimizing the properties of the nanoparticles are described below. However, one of skill in the art will understand that other assays and procedures may be readily performed.

Uptake and binding characteristics of nanoparticles may be evaluated in any suitable cell line, such as RAW 264.7, J774, jurkat, and HUVECs cells. The immunomodulatory role of nanoparticles may be assayed by determining the release of cytokines when these cells are exposed to varying concentrations of nanoparticles. Complement activation may be studied to identify which pathways are triggered using columns to isolate opsonized nanoparticles; e.g. as described in Salvador-Morales C, Zhang L, Langer R, Farokhzad O C, Immunocompatibility properties of lipid-polymer hybrid nanoparticles with heterogeneous surface functional groups, *Biomaterials* 30: 2231-2240, (2009). Because nanoparticle size is an important factor that determines biodistribution, Nanoparticles may be binned into various sizes (e.g., 20-40, 40-60, 60-80, 80-100, 100-150, and 150-300 nm) and tested according to size.

Any cell type appropriate for a therapeutic agent employed in a nanoparticle may be used to evaluate therapeutic efficacy or proper targeting. Assays appropriate for the therapeutic or pharmacologic outcome may be employed, as are generally understood or known in the art.

Biodistribution (bioD) and pharmacokinetic (PK) studies may be carried out in rats or other suitable mammals. For PK and bioD analysis, Sprague Dawley rats may be dosed with targeted or similar nanoparticles without the targeting groups, through a lateral tail vein injection. Animals may be sacrificed; and brain, heart, intestine, liver, spleen, kidney, muscle, bone, lung, lymph nodes, gut, and skin may be excised, weighed, homogenized to evaluate distribution. Tissue concentration may be expressed as % of injected dose per gram of tissue (% ID/g).

Therapeutic dosages of nanoparticles effective for human use can be estimated from animal studies according to well-known techniques, such as surface area or weight based scaling.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like.

As used herein, "disease" means a condition of a living being or one or more of its parts that impairs normal functioning. As used herein, the term disease encompasses terms such disease, disorder, condition, dysfunction and the like.

As used herein, "treat" or the like means to cure, prevent, or ameliorate one or more symptom of a disease.

As used herein, "bind," "bound," or the like means that chemical entities are joined by any suitable type of bond, such as a covalent bond, an ionic bond, a hydrogen bond, van der walls forces, or the like. "Bind," "bound," and the like are used interchangeably herein with "attach," "attached," and the like.

As used herein, a "derivative" of a compound is a compound structurally similar to the compound of which it is a derivative. Many derivatives are functional derivatives. That is, the derivatives generally provide a desired function similar to the compound to which it is a derivative. By way of example, triphenyl phosophonium (TPP) is described herein as a mitochondrial targeting moiety because it can accumulate, or cause a compound or complex (such as a nanoparticle) to which it is bound to accumulate, in the mitochondria. Accordingly, a functional derivative of TPP is a derivative of TPP that may accumulate, or cause a compound or complex to which it is bound to accumulate, in the mitochondria in a similar concentration as TPP (e.g., within about a 100 fold concentration range, such as within about a 10 fold concentration range).

In the following, non-limiting examples are presented, which describe various embodiments of representative nanoparticles, methods for producing the nanoparticles, and methods for using the nanoparticles.

EXAMPLES

Experimental
Cell Line and Cell Culture.

Human prostate cancer PC3, DU145 cells and RAW 264.7 macrophages were procured from the American type culture collection (ATCC). DU145 cells were grown at 37° C. in 5% $CO_2$ in Eagle's minimum essential medium (EMEM) supplemented with 10% fetal bovine serum (FBS) and 1% penicillin/streptomycin. PC3 cells were grown in Roswell Park Memorial Institute (RPMI) 1640 medium supplemented with 10% FBS and 1% penicillin/streptomycin. RAW 264.7 macrophages were cultured in RPMI media supplemented with 10% FBS and 1% penicillin/streptomycin. Cells were passed every 3 to 4 days and restarted from frozen stocks upon reaching pass number 20.

Synthesis of TPP-($CH_2$)5-COOH.

6-Bromohexanoic acid (0.5 g, 2.6 mmol) and triphenylphosphine (0.7 g, 2.7 mmol) were dissolved in acetonitrile (15 mL). The resulting mixture was heated to a reflux under nitrogen flow for 24 h. The solution was cooled to room temperature and concentrated under reduced pressure. The resulting viscous oil was washed with hexanes (2×15 mL) and diethyl ether (3×15 mL) to produce a white solid (0.85 g, 87% yield). $^1$H NMR ($CDCL_3$): δ 7.8-7.6 [m, 15], 3.52 [t, 2H], 2.3 [t, 2H], 1.61 [m, 6H] ppm. $^{13}$C NMR ($CDCl_3$): δ 175, 135.2, 133.4, 130.2, 118.5, 34.3, 29.5, 23.9, 22.8, 22.4, 22.1 ppm. $^{31}$P NMR ($CDCl_3$): δ 24.39 ppm.

Synthesis of SH-PEG-TPP.

SH-PEG-NH2 (0.2 g, 0.0571 mmol), TPP-(CH2)5-COOH (0.043 g, 0.1142 mmol), and 4-dimethylaminopyridine (DMAP) (0.014 g, 0.1142 mmol) were dissolved in 7 mL $CH_2Cl_2$, cooled to 0° C. while stirring, and a solution of dicyclohexylcarbodiimide (DCC) (0.024 g, 0.1142 mmol) in 1 mL $CH_2Cl_2$ was added. The mixture was warmed to room temperature and stirred overnight. The reaction by-product, dicyclohexylurea precipitated was filtered off and the filtrate was precipitated in chilled diethyl ether. The resulting solid was centrifuged at 5000 revolutions per minute (rpm) for 15 min. The supernatant was decanted and the resulting wet solid was lyophilized to result white solid. Yield: 50% (0.11 g). $^1$H NMR ($CDCl_3$): δ 7.82-7.57 [m, 15], 3.81 [m, 2H], 3.71 [m, 2H], 3.64 [m, 414], 2.88 [m, 2H], 1.73 [m, 2H] ppm. $^{13}$C NMR ($CDCl_3$): δ 207.15, 131.51, 131.48, 129.99, 129.9, 126.95, 126.83, 66.9 ppm. $^{31}$P NMR ($CDCl_3$): δ 24.63 ppm.

Synthesis of T and NT-AuNPs.

For T-AuNP synthesis, a solution of SH-PEG-TPP (0.1 g, 0.25 mmol) and SH-PEG-$NH_2$ (0.1 g, 0.25 mmol) were prepared in 15 mL $H_2O$ and gold(III) chloride trihydrate ($HAuCl_4.3H_2O$) (0.05 g, 0.12 mmol) was added. This mixture was vigorously stirred for 10 min until all of the gold salt was dissolved. The reduction was carried out by adding drop wise a freshly prepared aqueous solution of sodium borohydride (0.05 g, 1.2 mmol in 3 mL $H_2O$) with vigorous stirring and 15 mL of deionized (DI) water was then added to the mixture. After 24 h, the solution was dialyzed using a Spectra/Por® dialysis membrane of MW cutoff of 5,000 Da against $H_2O$ for 12 h. The water was changed every hour. The NPs were further purified by differential centrifugation at 7,000 rpm for 30 min. After centrifugation the supernatant was kept and the pellet was discarded to obtain monodispersed T-Au-NPs. The non-targeted NPs, NT-Au-NPs were prepared following the same synthetic method as mentioned for T-AuNPs using SH-PEG-NH2 (0.2 g, 0.5 mmol) and $HAuCl_4.3H_2O$ (0.05 g, 0.12 mmol).

Synthesis of T-3-BP-AuNPs and NT-3-BP-AuNPs.

3-BP was conjugated to the surface of the T-AuNP and NT-AuNP surface by amide coupling. 3-BP (30 mg, 0.18 mmol), N-hydroxysuccinimide (NHS) (39 mg, 0.12 mmol), and ethyl(dimethylaminopropyl) carbodiimide (EDC) (30 mg, 0.18 mmol) were dissolved in $H_2O$ (5 mL). 3-BP was allowed to activate for 6 h at 25° C. To this, T-AuNPs or NT-AuNPs (10 mg/mL, 5 mL) was added and stirred overnight at 25° C. NPs were purified by dialysis (MW cutoff of 2,000 Da) against water for 8 h changing the water every hour. NPs were lyophilized and freshly resuspended in nanopure water prior to use.

Determination of 3-BP Loading by GADPH Assay.

The activity of 3-BP on GAPDH was used to determine 3-BP loading on AuNPs using a KDalert™ GAPDH assay kit. GAPDH was treated with predetermined concentration of 3-BP to generate a standard curve. AuNPs (100 μL, 10 mg/mL) were treated with 1.0 mM potassium iodide (KI) to dissolve the gold core and then 10 μL of the NPs were then added to GADPH enzyme (10 μL, 0.133 U/mL) and subjected to the activity assay. The NP/GADPH enzyme suspension (10 μL) was then added to the KDalert™ master mix (90 μL) in a 96 well plate. The mixture was then gently shaken to ensure full mixing and the fluorescence was measured (excitation: 560 nm, emission: 590 nm).

Immune Response from NPs in RAW 264.7 Macrophages by ELISA.

RAW 264.7 macrophages were plated at a concentration of 50,000 cells/mL in 96 well plates and allowed to grow for 12 h. The cells were incubated with T-AuNP (10 mg/mL), NT-AuNp (10 mg/mL) for 24 h at 37° C. Additionally, LPS alone (100 ng/mL) was added to the macrophage culture to serve as a control. ELISA was performed on the supernatants against the pro-inflammatory cytokines IL-6 and TNF-α. Antibody coated plates were prepared by treating ELISA compatible thermo scientific Nunc 96-well plates with the antibody for 12 h at 4° C. and then blocked with 10% FBS in PBS for 1 h at room temperature followed by 5 washings with the washing buffer (1×PBS with 0.05% v/v Tween® 20). Macrophage supernatants (100 μL) were added to the plates and incubated for 2 h at room temperature, followed by 5 washes with the washing buffer and sequential incubations with the cytokine-biotin conjugate and streptavidin working solution. The substrate reagent containing 3,3',5,5' tetramethylbenzidine (100 μL) was then added to each well, incubated for 15 min in the dark, and the reaction was stopped by adding 50 μL stop solution containing 0.1 M $H_2SO_4$. The absorbance was recorded at 450 nm using a BioTek Synergy HT well plate reader.

Release of 3-BP from T-3BP-AuNP and NT-3-BP-AuNP.

The ability of 3-BP to be cleaved from the NP surface was tested by using proteases from *Streptomyces griseus* type XIV. T-3-BP-AuNP and NT-3-BP-AuNPs (10 mg/mL with respect to AuNP and 1.4 mM with respect to 3-BP) were treated with 0.5 mg/mL of protease in water for up to 6 h at 37° C. with gentle shaking. At a predetermined time point, the NPs were isolated by repeated centrifugations and resuspensions in nanopure water while discarding the supernatant each time at 12,000 rpm for 30 min. The resulting pellet was resuspended in 100 μL water and the amount of 3-BP was quantified by KDalert™ GADPH assay described above.

HK2 Binding Assay.

HK2 binding ability of T and NT 3-BP loaded AuNPs was tested by using human HK2 recombinant of molecular mass 104.1 kDa expressed in *Escherichia coli*. T-AuNPs, NT-AuNPs, T-3-BP-AuNP, and NT-3-BP-AuNPs (10 mg/mL with respect to AuNP and 1.4 mM with respect to 3-BP) were treated with 1 μL solution of 1.0 mg/mL of HK2 (in 20 mM Tris pH 8.0 and 10% glycerol) for 1 h at 37° C. HK2 bound NPs were then centrifuged at 12000 rpm for 30 min and supernatants were discarded to remove unbound HK2. This process was repeated 3 times and finally the NP pellet obtained was resuspended in water. BCA assay directly on the HK2-bound to AuNP did not show any signal. Therefore, the Au core was dissolved using 1 mM KI and BCA assay was performed to quantify the amount of HK2 bound to 3-BP. A standard curve was constructed using bovine serum albumin (BSA). For protease mediated cleavage of HK2-loaded AuNPs, these NPs were treated with proteases for 12 h and subsequently BCA assay was performed.

Quantification of AuNPs in the Mitochondrial Compartments.

PC3 cells were grown at a density of 5×105/mL cells in 30 mL RPMI media overnight in T-150 flask. The media was changed and T-AuNPs or NT-AuNPs were added (1 mg/mL) and incubated for 12 h. The media was changed and the cells were rinsed with 1× phosphate buffered saline (PBS) (3×). The cells were isolated by trypsinization and centrifuged for 3 min at 1,800 rpm. The final cell suspension was resuspended in reagent A from the mitochondria isolation kit for mammalian cells and incubated on ice for 2 min. After 2 min, reagent B (10 μL) was added and incubated on ice for 5 min, vortexing each min. These cells were treated with reagent C and the cells were centrifuged at 700×g for 10 min. The resulting supernatant was collected containing the mitochondrial and cytosolic fractions. This was further centrifuged at 12,000×g for 15 min at 4° C. to yield a mitochondrial pellet and the cytosolic supernatant. The resulting pellet was further purified with a washing and centrifugation at 12,000×g for 5 min to yield the mitochondrial fraction. These fractions were analyzed for the amount of gold by ICP-MS and the amount of protein recovered by BCA assay. To evaluate the exact location of the T-AuNPs and T-3-BP-AuNPs within the mitochondria, the mitochondria were further fractionated. PC3 cells were grown at a density of 5×10$^5$/mL cells in 30 mL RPMI media overnight in T-150 flask. The media was changed and TAuNPs or T-3-BP-AuNPs were added (1 mg/mL) and incubated for either 4 or 12 h. After the given time, the cells were trypsinized and repeatedly washed with PBS at 1,800 rpm for 3 min. The mitochondria were isolated as described above. This was further subfractionated into the OMM, the intermembrane space, the IMM, and the matrix. The freshly isolated PC3 mitochondria in PBS (1×) were incubated with protease inhibitor (0.125 mg/mL) and 0.6% digitonin for 10 min on ice. Immediately after incubation, the mitochondria were centrifuged at 10,000×g for 10 min at 4° C. The supernatant (SN-I) contained the OMM fraction and the interstitial membrane space. The pellet was resuspended in 150 mmol/L KCl, protease inhibitor (0.125 mg/mL) and incubated on ice for 10 min. This was centrifuged at 10,000×g for 10 min at 4° C. The supernatant, which contained the mitochondrial matrix, was collected. To this, 50 μL of 1× cell lysis buffer (30 mM Tris-HCl, 0.1 mM EDTA, 20% w/v sucrose) was added. This was subsequently sonicated and centrifuged at 10,000 g for 15 min at 4° C. The supernatant (SN-II) was collected, containing the purified IMM fraction and matrix. SN-I and SN-II were centrifuged at 105,000×g for 60 min. The pellet from SN-I contained the OMM fraction and the supernatant contained the interstitial membrane space. The pellet from SN-II was resuspended in PBS containing Lubrol WX (0.5 mg/mL), 37% sucrose and incubated for 15 min on ice. This was once again centrifuged at 105,000×g for 60 min at 4° C. The pellet was collected containing the IMM fraction and the supernatant contained the matrix. The collected fractions were analyzed for Au concentration by ICP-MS. A BCA assay was performed on all the fractions in order to calculate the Cd (ng)/protein (pg).

MTT Assay and Data Analysis.

Cytotoxicity profiles of T-AuNPs, NT-AuNPs, T-3-BPAuNPs, NT-3-BP-AuNPs, and 3-BP were studied using the MTT assay against prostate cancer PC3 and DU145 cell lines. Cells (2000 cells/well) were seeded on a 96-well plate in 100 µL of desired medium and incubated for 24 h. The cells were then treated with different constructs at varying concentrations and incubated for 12 h at 37° C. and the media was changed. The cells were further incubated for additional 60 h at 37° C. under 5% CO2. For photothermal MTT studies, after 4 h treatment of cells with NPs, the cells were irradiated with 660 nm laser (power 20.0 mV) light with a fiber optics for 1 min per well and the irradiated cells were incubated for 12 h at 37° C., followed by a media change and further incubation for 60 h. The cells were then treated with 20 µL of MTT (5 mg/mL in PBS) for 5 h. The medium was removed, the cells were lysed with 100 µL of DMSO, and the absorbance of the purple formazan was recorded at 550 nm using a Bio-Tek Synergy HT microplate reader and background absorbance was measured at 800 nm. Each well was performed in triplicate and each experiment was repeated three times. Cytotoxicity was expressed as mean percentage increase relative to the unexposed control±standard deviation (SD). Control values were set at 0% cytotoxicity or 100% cell viability. Cytotoxicity data (where appropriate) was fitted to a sigmoidal curve and a three parameters logistic model used to calculate the IC50, which is the concentration of chemotherapeutics causing 50% inhibition in comparison to untreated controls. The mean IC50 is the concentration of agent that reduces cell growth by 50% under the experimental conditions and is the average from at least three independent measurements that were reproducible and statistically significant. The IC50 values were reported at ±95% confidence intervals. This analysis was performed with GraphPad Prism (San Diego, U.S.A).

Apoptosis Detection by Flow Cytometry.

PC3 cells were plated at a density of $1 \times 10^6$ cells/mL and allowed to grow for 14 h. Media was changed and cells were treated with T-AuNP (1 mg/mL), NT-AuNP (1 mg/mL), T-3-BP-AuNP (14.1 µg/mL with respect to NP, 10 µM with respect to 3-BP), NT-3-BP-AuNP (13.7 µg/mL with respect to NP, 10 µM with respect to 3-BP), free 3-BP (10 µM or 1 mM) for 6 h at 37° C. As positive controls, etoposide (100 µM, incubation time: 12 h) for apoptosis and $H_2O_2$ (1 mM, incubation time: 45 min) for necrosis were used. For apoptosis detection after laser treatment, cells were treated with T-AuNP (1 mg/mL), NT-AuNP (1 mg/mL), T-3-BP-AuNP (14.1 µg/mL with respect to NP, 10 µM with respect to 3-BP), NT-3-BP-AuNP (13.7 µg/mL with respect to NP, 10 µM with respect to 3-BP), free 3-BP (10 µM) for 4 h at 37° C., irradiated with laser of 660 nm for 1 min, and further incubated for 12 h. Cells were trypsinized, washed 3 times with cold 1×PBS, and centrifuged at 1800 rpm for 3 min, and the supernatants were discarded. Cells were counted and resuspended in 1× annexinbinding buffer at a density of ~$1 \times 10^6$ cells/mL preparing a sufficient volume to have 100 µL per assay. To 100 µL of cell suspension, 5 µL Alexa Fluor® 488 annexin V and 1 µL 100 µg/mL PI working solution were added, incubated for 15 min at room temperature, followed by addition of 400 µL 1× annexin-binding buffer, gently mixing in ice, and the samples were analyzed on the flow cytometer immediately.

Lactate Determination.

PC3 cells were seeded at a density of $1 \times 10^6$ cells/mL and allowed to grow for 12 h at 37° C. under 5% $CO_2$. Cells were treated with T-AuNP (1 mg/mL), NT-AuNP (1 mg/mL), T-3-BP-AuNP (14.1 µg/mL with respect to NP, 10 µM with respect to 3-BP), NT-3-BP-AuNP (13.7 µg/mL with respect to NP, 10 µM with respect to 3-BP), free 3-BP (10 µM) for 6 h at 37° C. After 6 h, the media was removed and the cells were homogenized. The lysate and the media supernatant were added to the enzyme and substrate working reagent mixture and incubated for 30 min. Lactate concentration was measured using Bio-Tek Synergy HT microplate reader at 450 nm and comparing to a standard curve.

CellTiter-Glo® Luminescent ATP Quantification.

PC3 cells were seeded at a density of $1 \times 10^6$ cells/mL in a 12 well plate and allowed to grow for 12 h at 37° C. under 5% $CO_2$. Cells were treated with T-AuNP (1 mg/mL), NT-AuNP (1 mg/mL), T-3-BP-AuNP (14.1 µg/mL with respect to NP, 10 µM with respect to 3-BP), NT-3-BP-AuNP (13.7 µg/mL with respect to NP, 10 µM with respect to 3-BP), free 3-BP (10 µM) for 6 h at 37° C. in 5% $CO_2$ atmosphere. Control wells containing medium without cells were used to obtain background luminescence value. Plates were then equilibrated at room temperature for ~30 min. A volume of CellTiter-Glo reagent equal to the volume of cell culture medium present in each well was added, this mixtures were mixed for 2 min in a shaker to induce cell lysis. The plates were incubated at room temperature for additional 10 min to stabilize luminescent signal. Luminescence was recorded using a plate reader. ATP quantification was carried out from a standard curve using ATP disodium salt hydrate.

Bioenergetic Assay.

Prior to the assay, XF sensor cartridges were hydrated. To each well of an XF utility plate, 1 mL of Seahorse Bioscience calibrant was added and the XF sensor cartridges were placed on top of the utility plate, and kept at 37° C. incubator without $CO_2$ for a minimum of 12 h. PC3 cells were cultured in XF24-well cell culture microplates (Seahorse Bioscience) at a density of $5 \times 10^4$ cells/well (0.32 cm2) in 200 µL growth medium and then incubated for 24 h at 37° C. in 5% CO2 atmosphere. The three key parameters of glycolytic function: glycolysis, glycolytic capacity, and glycolytic reserve were assessed using a Seahorse XF glycolysis stress kit. After the cells were attached, an additional 100 µL growth medium was added and the cells were incubated for 24 h at 37° C. in 5% $CO_2$ atmosphere. The cells were treated with T-3-BPAuNP (10 µM with respect to 3-BP), NT-3-BP-AuNP (10 µM with respect to 3-BP), and 3-BP (10 µM) for 6 h at 37° C. in 5% $CO_2$ atmosphere. After 6 h, all but 50 µL of the culture medium was removed from each well and the cells were rinsed two times with 600 µL of XF stress test glycolysis optimization medium pre-warmed to 37° C. and finally 610 µL of glucose depleted optimization medium was added to each well and the plate was placed at 37° C. without $CO_2$ for 1 h prior to assay. The OCR and the ECAR were measured simultaneously for 16 min to establish a baseline rate. Glycolysis, glycolytic capacity, and glycolytic reserve were calculated by subtracting the average rates before and after the addition of glucose (10 mM), ATP synthase inhibitor oligomycin (1.0 µM), and 2-deoxy-D-glucose (2-DG) (100 mM). These three compounds were injected consecutively with specific time gap and ECAR values were measured after each injection. Different parameters of respiration: basal respiration, coupling efficiency, and spare respiratory capacity were investigated by using Seahorse XF-24 cell Mito Stress Test Kit. PC3 cells were plated and treated with different constructs as mentioned above. After 6 h incubation with the constructs, the media was changed as above with the optimization media supplemented with sodium pyruvate, L-glutamine, and D-glucose to a final volume of 500 µL. Different parameters of respiration were calculated by subtracting the average respiration rates before and after the addition of the electron transport inhibitors oligomycin (1.0 µM), FCCP (1.0 µM), an ionophore that is a mobile ion carrier, and a mixture of antimycin-A 1.0 μM) which is a complex III inhibitor and rotenone (1.0 μM), a mitochondrial inhibitor that prevents the transfer of electrons from the Fe-S center in Complex I to ubiquinone. The parameters calculated included: basal respiration (baseline respiration minus antimycin-A post injection respiration), ATP turnover (baseline respiration minus oligomycin post injection respiration), maximal respiratory capacity (FCCP stimulated respiration minus antimycin-A post injection respiration) and reserve respiratory capacity (FCCP stimulated respiration minus baseline respiration). Test articles on each well had five replicates.

Results and Discussion

AuNPs for Targeted Delivery of 3-BP.

Figure 1B:
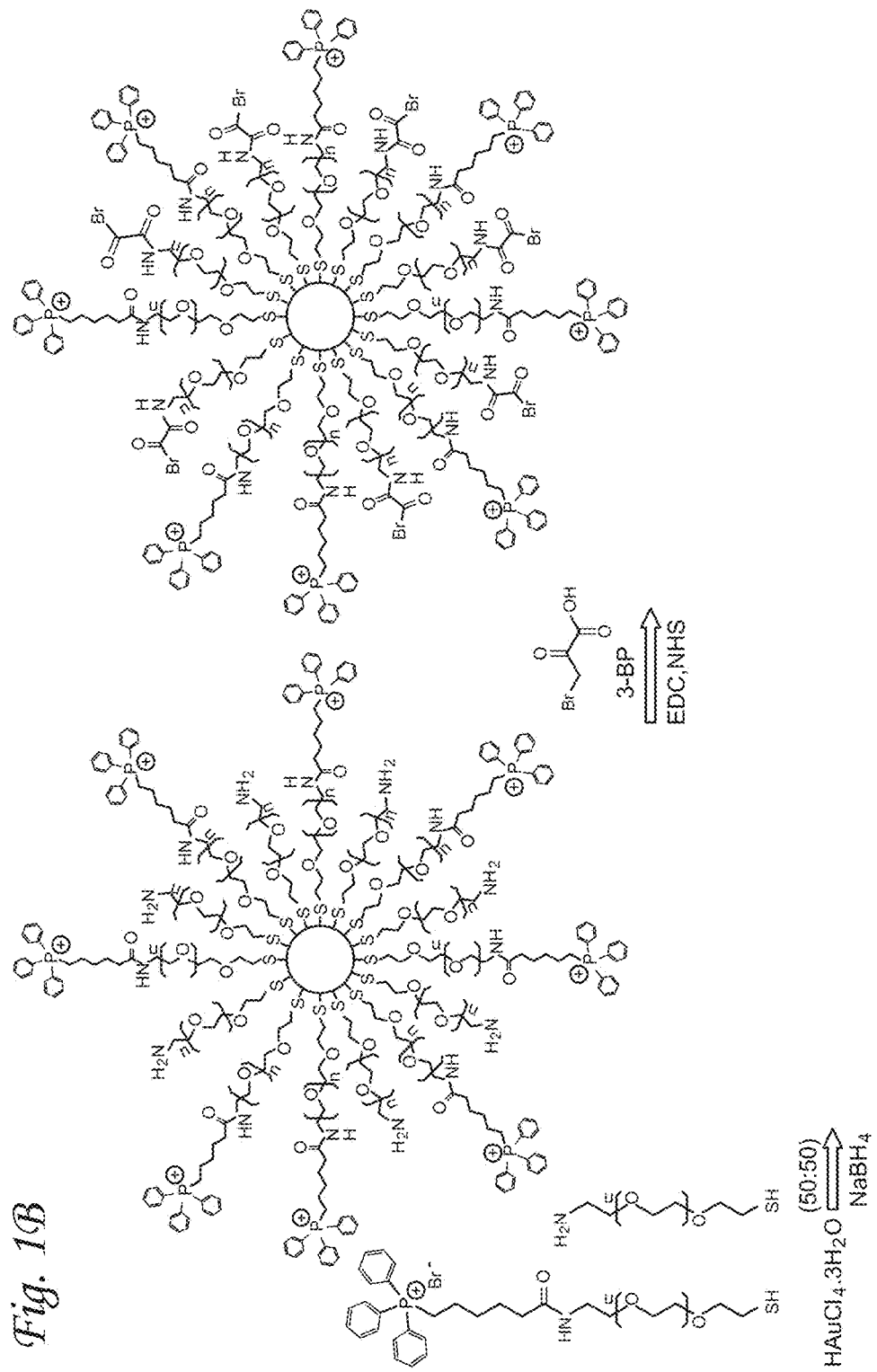
Figure 2A:
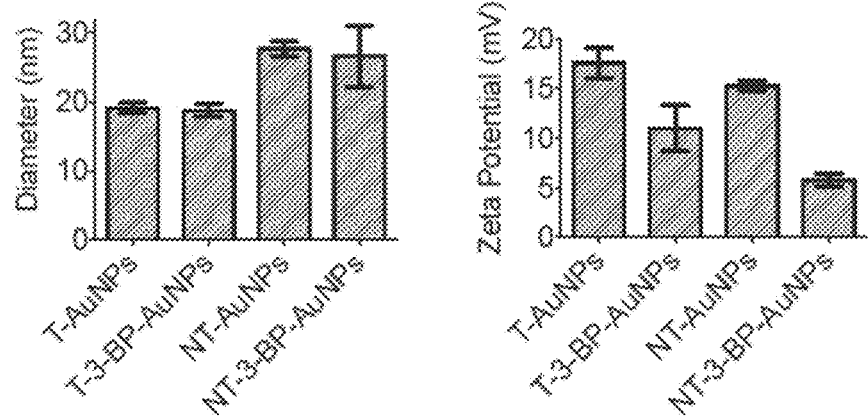
FIG. 2: (A) Characterization of different AuNPs by DLS. (B) TEM of AuNPs. (C) Quantification of 3-BP by GADPH assay. (D) Non-immunogenic behavior of NT and TAuNPsby ELISA.
Figure 2B:
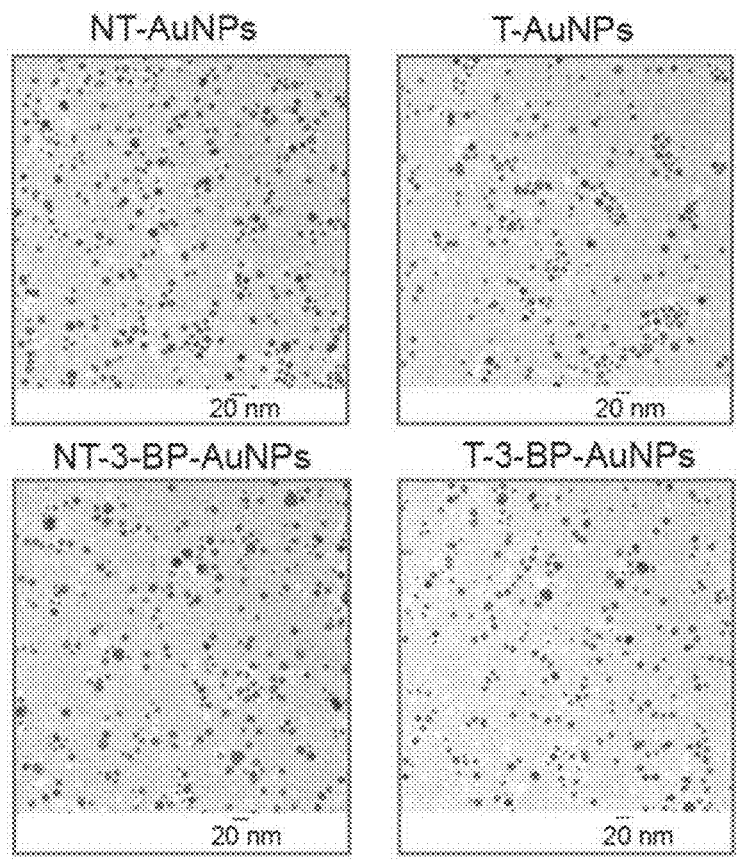

AuNPs are widely used in delivery of therapeutics due to their unique surface chemistry, tunable size, shape, and optical properties. However, one of the important issues in clinical translation of AuNPs is their toxicological effect. A recent study demonstrated that unmodified citrate coated AuNPs can cause inhibition of cell proliferation in a concentration and size dependent manner. Therefore, it may be important to design a biocompatible surface functionalized AuNP for delivery of 3-BP inside the mitochondria. Polyethylene glycol (PEG) is often used to protect surfaces from nonspecific interactions with biomolecules. To deliver 3-BP inside the mitochondria, we constructed AuNPs covered with lipophilic cationic -TPP moieties attached to PEG. The lipophilic TPP cations easily permeate lipid bilayers driven by the plasma membrane potential (−30 to −60 mV) to enter cytoplasm and then concentrated several hundred-fold into mitochondria by the large mitochondrial membrane potential ($\Delta\psi m$) (−150 to −180 mV) maintained across the inner mitochondrial membrane (IMM). To construct T-AuNPs, we synthesized TPP-PEG-SH by reacting $NH_2$-PEG-SH with TPP-$(CH_2)_5$—COOH (FIG. 1). The -TPP group in TPP-PEG-SH allowed for mitochondria targeting and the —SH acted as anchoring group to AuNP surface. T-AuNPs were synthesized through the reduction of $HAuCl_4.3H_2O$ and simultaneous stabilization with a mixture of $NH_2$-PEG-SH and TPP-PEG-SH. The amine groups from T-AuNPs were conjugated with 3-BP using a standard amide coupling reaction to result T-3-BP-AuNPs (FIG. 1). To investigate the advantages of delivering 3-BP inside mitochondria, we constructed a non-targeted system, NT-AuNP, as a control. NT-AuNPs were constructed from $HAuCl_4.3H_2O$ using $NH_2$-PEG-SH and the amine groups were used to conjugate 3-BP to generate NT-3-BP-AuNPs. AuNPs were characterized by dynamic light scattering (DLS), zeta potential measurements, and by transmission electron microscopy (TEM) (FIGS. 2A, 2B). The intensity-weighted average or the Z average of these NPs were mostly between 20 to 30 nm and were narrowly distributed. In our previous studies, we demonstrated that positively charged NPs of suitable size have the ability to enter mitochondria of cells, whereas negatively charged particles or NPs which are not highly positively charged or larger in size mostly distribute in the cytosols. Zeta potential measurements indicated that TAuNP surface is positively charged and conjugation of 3-BP on the surface lowered the potential by ~6 mV. Non-targeted NPs with surface —$NH_2$ groups showed positive zeta potential and conjugation of 3-BP diminished the positive charge by ~10 mV. The small sizes and high positively charged surface coated with highly lipophilic cationic TPP moieties in T-3-BP-AuNPs played significant roles in their navigation to the mitochondria. The morphology of these NPs was mostly spherical as demonstrated by TEM (FIG. 2B). To demonstrate the versatility in biomedical applications, the dispersion stability of these AuNPs was evaluated by freeze drying the NPs and assessing the formation of aggregates and change in color upon making aqueous suspension at a concentration of 10 mg/mL. No visible aggregation or changes in the color was observed and the resuspended NPs demonstrated similar sizes and zeta potential. The T and NT-AuNPs showed surface plasmon band at 540 and 523 nm, respectively. Upon conjugation of 3-BP on the surface of both T and NT-AuNPs, no changes in the diameter, no broadening or red shift of the surface plasmon band was observed indicating that no aggregation of AuNPs occurred during surface modification.

Figure 2C:
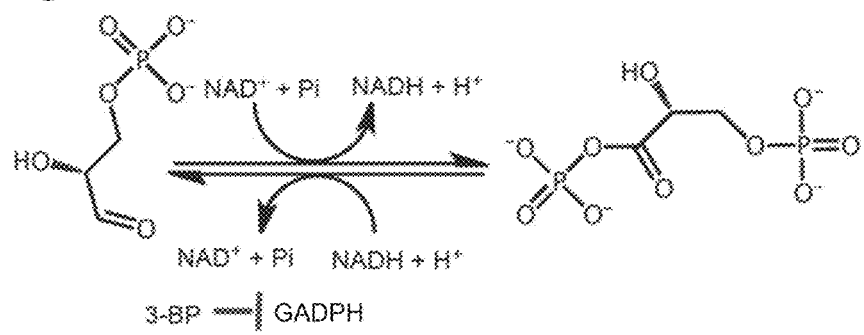
Figure 2C:
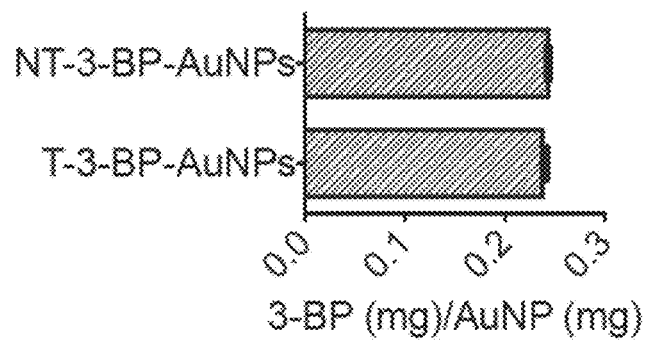

It is challenging to quantify 3-BP in AuNPs using conventional analytical methods. We therefore devised an enzyme inhibition assay to quantify coupling efficiency of 3-BP on NP surface based on the fact that glyceraldehyde-3-phosphate dehydrogenase (GAPDH) is an intracellular target of 3-BP (FIG. 2C). Pyruvylation of GADPH by 3-BP causes inhibition of the enzymatic function. The enzyme activity of GAPDH can be determined using a KDalert™ GAPDH assay kit. Generation of a standard curve by treating GAPDH with known concentrations of 3-BP, dissolution of Au core of T and NT-3-BP-AuNPs with potassium iodide (KI), and subsequent treatment with GADPH allowed us to quantify amount of 3-BP present on the NP surface (FIG. 2B). Similar coupling efficiencies of 3-BP on the surface of T and NTAuNPs were noted (~8%, Table S1).

Figure 2D:
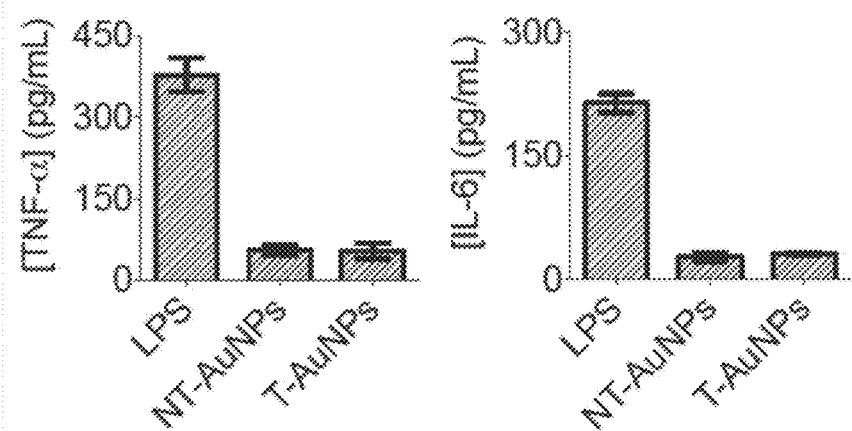

Macrophages are one of the principal immune effector cells, hence the immunological response of RAW264.7 macrophage cells when exposed to T and NT-AuNPs was studied by following the production of pro-inflammatory cytokines, tumor necrosis factor alfa (TNF-α) and interleukin-6 (IL-6), using enzyme-linked immunosorbent assay (ELISA) (FIG. 2D). Neither the control cells nor the cells treated with T and NT-AuNPs showed any secretion of either TNF-α or IL-6. Both the cytokines were detected in the cells treated with bacterial lipopolysaccharide (LPS) as control (FIG. 2D). These results indicated that AuNPs do not elicit immunological response and do not induce production of pro-inflammatory cytokines even at high concentrations of 10 mg/mL.

Protease Dependent Release of 3-BP from AuNPs.

3-BP can be a multitasking agent if it can be delivered to cancer cell, its mitochondria, and released at the target sites. For inhibition of cytosolic glycolysis, 3-BP directly alkylates HK2 by reacting with the —SH groups from Cys 158 and Cys 606 which are present in the enzyme active sites. The terminal step of OXPHOS in making ATP in the mitochondria requires an ATP synthase (F(0)F(1)) comprised of two motors, PIC and ANC which carry phosphate and adenine nucleotide for ATP synthesis, respectively. 3-BP alkylates PIC and ANC that results in halting the final step of OXPHOS. Conformational changes associated with VDAC bound HK2 leads to its direct dissociation from the mitochondria that promotes mitochondrial injury provoked by pro-apoptotic proteins. Specific release of apoptosis-inducing factor (AIF), cytochrome c from the mitochondria to cytosol leads to eventual cell death. For successful execution of these processes, 3-BP needs to be released from the AuNPs at the target sites. In T-3-BP-AuNPs and NT-3-BP-AuNPs, 3-BP was conjugated to the AuNP surface via amide bonds in order to take advantage of the cellular proteases to catalyze the hydrolysis of these linkages to release 3-BP. Moreover, various proteases within mitochondria regulate mitochondrial biogenesis to ensure complete degradation of excess or damaged proteins. To test 3-BP release profile from the AuNPs, T-3-BP-AuNP and NT-3-

Figure 3A:
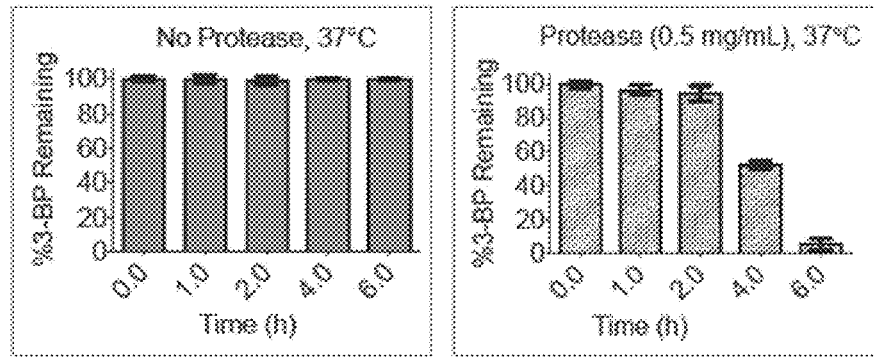
FIG. 3: (A) Protease dependent release of 3-BP from T and NT-AuNPs. (B) HK2 binding profile of T-3-BP-AuNPs and NT-3-BP-AuNPs. (C) Mitochondrial and cytosolic distribution of T-AuNPs and NT-AuNPs and time-dependent distribution of T-AuNPs and T-3-BP-AuNPs in different mitochondrial.
Figure 3A:
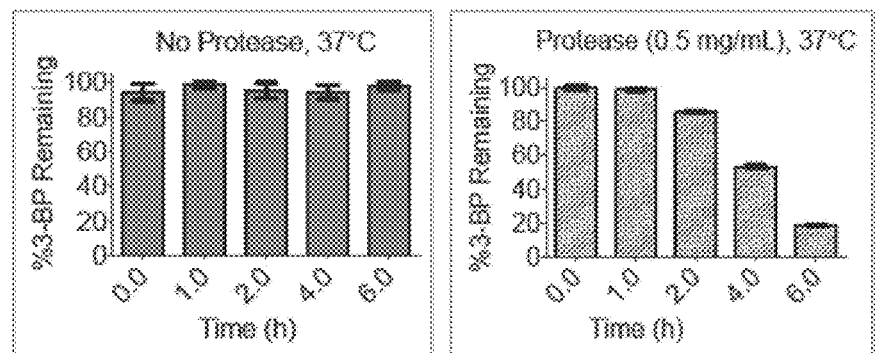

BPAuNP were treated with proteases from *Streptomyces griseus* type XIV at 37° C. and the concentration of 3-BP released was followed using the GADPH assay (FIG. 3A). In the absence of protease, no release of 3-BP from T-AuNP or NT-AuNP was observed under these conditions. In the presence of 0.5 mg/mL protease, ~50% of 3-BP was released from both T and NT-AuNPs in 4 h and >80% release of 3-BP was observed after 6 h. Thus, based on these data, we believe that some 3-BP will be released in the cytosol by the cytosolic proteases and T-3-BPNPs that will enter mitochondria will take advantage of high concentration of proteases in the mitochondrial matrix for 3-BP release (FIG. 3A).

HK2 Binding Affinity of Released 3-BP from T- and NT-AuNPs.

Figure 3B:
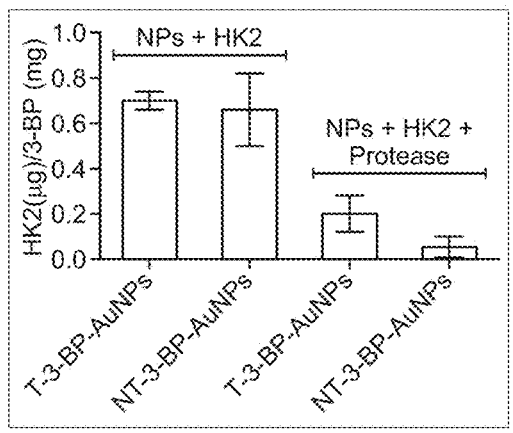

The ability of 3-BPs from T-3-BP-AuNPs and NT-3-BP-AuNPs to covalently modify HK2 was tested using human HK2 recombinant of molecular mass 104.1 kDa expressed in *Escherichia coli*. Incubation of HK2 with T-3-BP-AuNPs and NT-3-BP-AuNPs, quantification of 3-BP-bound HK2 using the bicinchoninic acid (BCA) assay after dissolving the Au core with KI indicated that 3-BP from both T and NT-AuNPs has the ability to covalently bind to HK2 (FIG. 3B). Incubation of HK2 bound AuNPs with protease and subsequent protein quantification by BCA assay showed less protein concentration, which further confirmed that, 3-BP covalently modified HK2 (FIG. 3B). T and NT-AuNPs without 3-BP did not show presence of any protein under these conditions. These data rule out the possibility that HK2 are simply adsorbed on the surface without interaction with 3-BP.

Intracellular Location of T-3-BP-AuNPs.

Figure 3C:
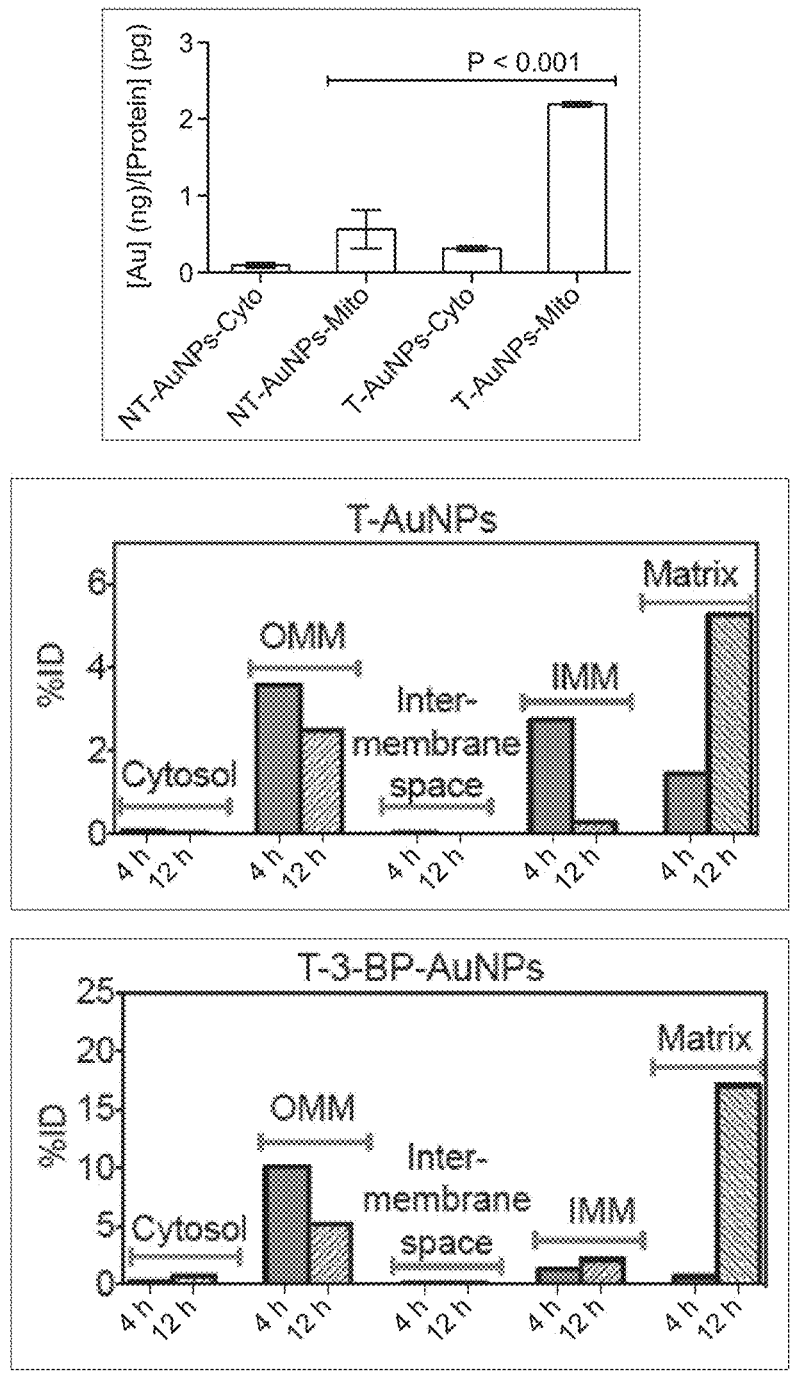

3-BP has several intracellular targets, thus the distribution of the T-AuNPs is the key factor in determining the efficacy of 3-BP. Where T-AuNPs or NT-AuNPs are located is essential information for understanding intracellular compartmentation of 3-BP. We first investigated distribution of NT and T-AuNPs in the mitochondria and cytosol in prostate cancer (PCa) PC3 cells. Treatment of these cells with the NPs for 12 h, isolation of mitochondrial (mito) and cytosolic (cyto) fractions, and quantification of gold by inductively coupled plasma mass spectrometry (ICP-MS) indicated that the overall uptake of T-AuNPs is higher than that of NT-AuNPs (FIG. 3C). Most of T-AuNPs are associated with the mitochondria. Only a small fraction of NT-AuNPs were associated with the mitochondria which might be attributed from the positively charged amine groups on the surface of these NPs. Highly lipophilic cationic -TPP groups are responsible for greater association of T-AuNPs with the mitochondria. We next assessed the exact location of T-AuNPs and T-3-BPAuNPs inside the mitochondria and investigated the time dependency of NP accumulation in different mitochondrial compartments. PC3 cells were treated with T-AuNPs and T-3-BP-AuNPs for two time points, 4 h and 12 h, and mitochondrial sub-fractions, OMM, IMM, intermembrane space, and matrix were isolated from the treated cells at both the time points, and gold was quantified in these fractions by ICP-MS (FIG. 3C). T-AuNPs and T-3-BP-AuNPs show very similar patterns in their mitochondrial distribution; however, the overall concentrations of T-3-BP-AuNPs were higher in the mitochondrial compartments compared to the T-AuNPs without any 3-BP. At early stage after 4 h incubation, both T-AuNPs and T-3-BP-AuNPs were found in the OMM and at 12 h, almost all T-AuNPs and T-3-BP-AuNPs were located inside the matrix. These observations indicated that the T-3-BP-AuNPs distributed in the OMM will be able to modify HK2 bound to VDAC. Complete localization of T-3-BP-AuNPs at 12 h might also be due to opening of the VDACs upon deactivation of HK2 by 3-BPs. Intra-mitochondrial distribution patterns of T-3-BP-AuNPs in a time dependent manner indicated that 3-BP delivered by T-AuNPs will be able to attack all of its intracellular targets for maximum efficacy.

Anti-Proliferative Effects of T-3-BP-AuNPs.

Figure 4A:
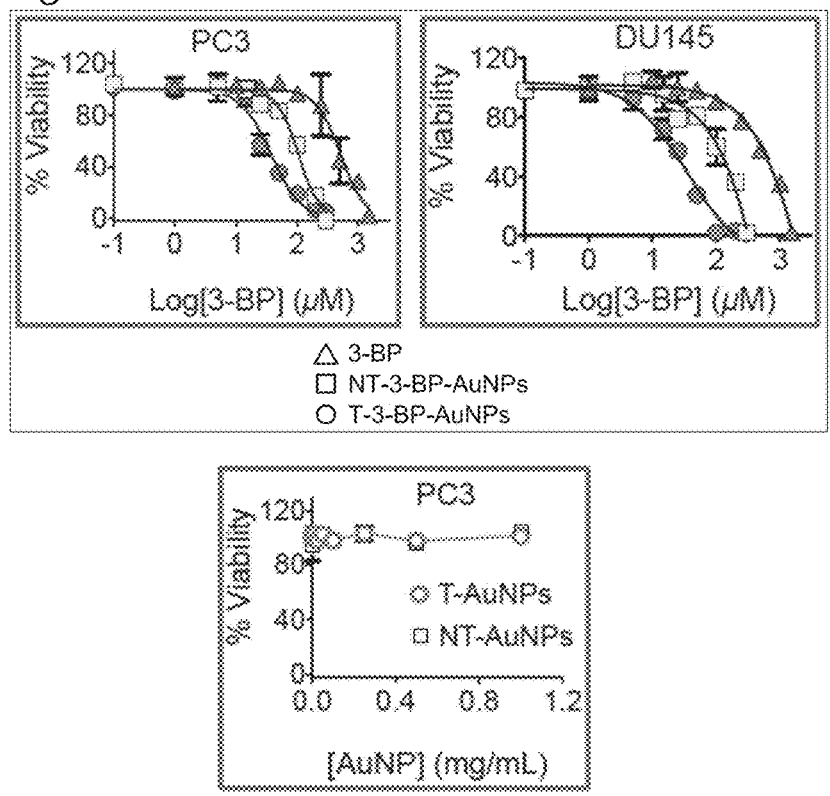
FIG. 4: (A) Cells viability in PC3 and DU145 cells after treatment with T-AuNPs, NTAuNPs, 3-BP, T-3-BP-AuNPs, NT-3-BP-AuNPs. Cell viability was assessed by the MTT assay after treatment with the indicated concentrations of the test articles for 72 h. The data are mean±SD (n=3 wells). (B) Cells viability in PC3 cells after treatment with TAuNPs, NT-AuNPs, 3-BP, T-3-BP-AuNPs, NT-3-BP-AuNPs followed by 660 nm laser radiation for 1 min/well. The data are mean±SD (n=3 wells). (C) (Top) Apoptotic patterns induced in PC3 cells upon treatment with T-AuNP (1 mg/mL), NT-AuNP (1 mg/mL), T-3-BP-AuNP (14.1 µg/mL with respect to NP, 10 µM with respect to 3-BP), NT-3-BP-AuNP (13.7 µg/mL with respect to NP, 10 µM with respect to 3-BP), free 3-BP (10 µM) for 6 h at 37° C. in the dark. (Bottom) Apoptosis induced in PC3 cells upon treatment with T-AuNP (1 mg/mL), NT-AuNP (1 mg/mL), T-3-BP-AuNP (14.1 µg/mL with respect to NP, 10 µM with respect to 3-BP), NT-3-BP-AuNP (13.7 µg/mL with respect to NP, 10 µM with respect to 3-BP), free 3-BP (10 µM) for 4 h at 37° C., followed by irradiation with 660 nm laser for 1 min, and further incubation for 12 h. Annexin V-PI assay results are presented in quadrants as analyzed by flow cytometry. The x-axis represents Alexa Fluor® 488 Annexin V and the y-axis represents PI. Live cells accumulate in Q4 (Annexin V and PI negative), cells undergoing apoptosis accumulate in Q3 (Annexin V positive and PI negative), cells in end-stage apoptosis or necrotic stage accumulate in Q2 (Annexin V and PI positive).
Figure 4B:
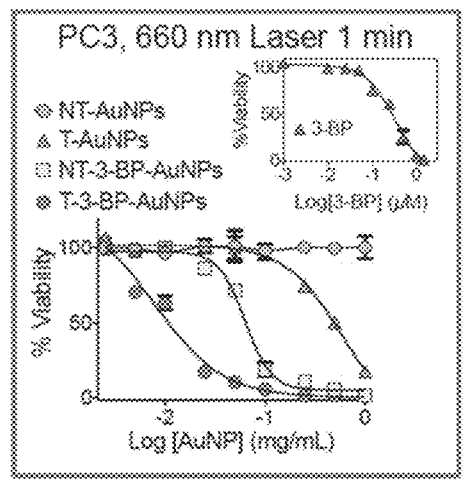

We determined the effect of AuNPs on proliferation of two different PCa cell lines-PC3 and DU145 cells by the 344,5-dimethylthiazol-2-yl)-2,5-diphenyltetrazolium bromide (MTT) assay. The widely used PCa cell lines PC3 and DU145 show differences in their metabolic phenotype. Both DU145 and PC3 lines have higher rates of lactate production, however these cell lines differed in glycolytic rate. PC3 cells show higher mRNA levels for glycolytic enzymes. The glycolytic reliance of PC3 and DU145 cells is believed to be due to OXPHOS insufficiency and the reduced reliance on OXPHOS is due to a mitochondrial dysfunction. T-3-BP-AuNPs exhibited highest efficacy in inhibiting proliferation of both PC3 and DU145 cells, NT-3-BP-AuNPs demonstrated significantly reduced inhibition compared to the T-3-BP-AuNPs, and free 3-BP showed only a modest inhibition (FIG. 4A, Table 1). No inhibition in cell growth was observed with T-AuNPs and NT-AuNPs without 3-BP (FIG. 4A, Table 1). These findings indicated preclinical proof of the concept that delivery of 3-BP to mitochondria using NP system results in enhanced uptake and cytotoxicity. Moreover, T-3-BP-AuNPs demonstrated an enhanced cytotoxic activity when combined with a 660 nm laser irradiation than NT-3-BP-AuNPs or free 3-BP plus laser treatment. It was interesting to note that T-AuNPs without any 3-BP showed an enhanced cytotoxicity under laser irradiation, whereas NT-AuNPs did not show any significant toxicity in presence of photo-irradiation (FIG. 4B, Table 1). These findings suggested that the higher accumulation of T-AuNPs inside mitochondria might be responsible for its toxicity under photo-irradiation by inducing local mitochondrial damage. These results together support that T-AuNP is highly effective for selective delivery of 3-BP and T-3-BP-AuNPs demonstrated the effects of targeted chemotherapy and photothermal effect.

TABLE 1

$IC_{50}$ with standard deviation calculated from three independent experiments

|  | PC3[a] (μM) | DU145[a] (μM) | PC3 + Laser[b] (mg/mL) |
|---|---|---|---|
| T-AuNPs | N/A | N/A | 0.55 ± 0.09 |
| NT-AuNPs | N/A | N/A | N/A |
| 3-BP | 271 ± 9 | 541 ± 37 | N/A |
| T-3-BP-AuNPs | 13 ± 3 | 28 ± 8 | 0.010 ± 0.003 |
| NT-3-BP-AuNPs | 45 ± 6 | 109 ± 7 | 0.060 ± 0.003 |

[a]With respect to 3-BP;
[b]With respect to AuNP

Figure 4C:
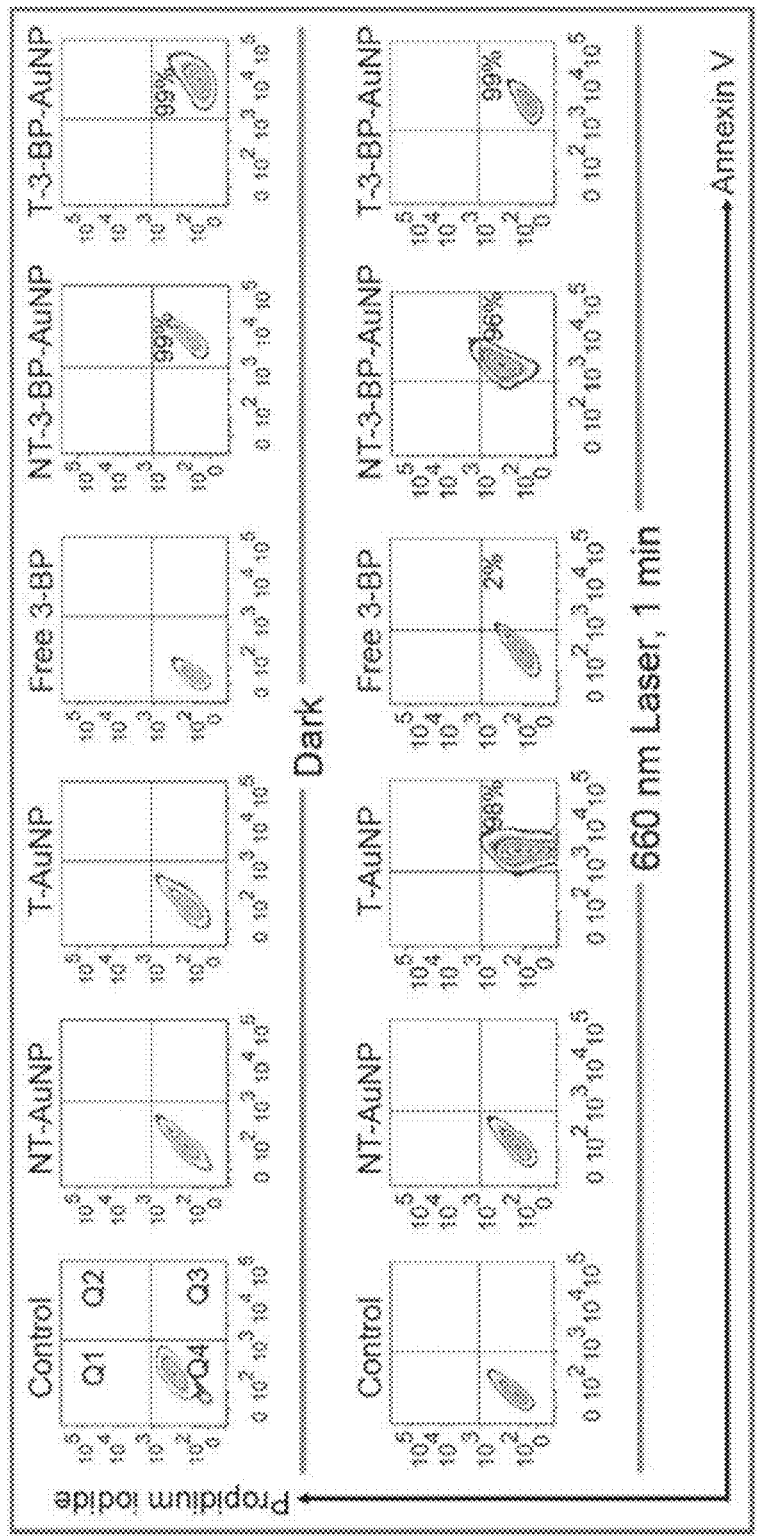

Induction of apoptosis is an important mechanism whereby 3-BP can suppress tumorigenesis. The pro-apoptotic effect of T-3-BP-AuNPs, NT-3-BP-AuNPs, and free 3-BP was studied in PC3 cells using Alexa Fluor® 488 Annexin V-propidium iodide (PI) assay by flow cytometry both in the dark and in presence of 660 nm laser irradiation for 1 min (FIG. 4C). Treatment of PC3 cells with T- and NT-3-BP-AuNPs showed increased percentage of apoptotic cells from 0% in control group to 99%. No necrotic cell population was noted in T and NT-3-BP-AuNP treated cells. Free 3-BP under same conditions with a concentration of 10 μM was unable to show any apoptotic activity, however at a much higher concentration of 1 mM, significant apoptosis was observed in 3-BP treated PC3 cells. Under photo-irradiation of PC3 cells for 1 min with a 660 nm laser, T-AuNPs, with the ability to accumulate in the mitochondria, showed apoptotic activity. The apoptosis inducing properties of T-3-BP-AuNPs and NT-3-BP-AuNPs were found to be very similar (FIG. 4C). Our data thus suggested that 3-BP can promote apoptosis at a much lower concentration when delivered with a mitochondria-targeted delivery system and use of AuNPs as delivery system further enhances its activity by utilizing photothermal activity of gold nanocrystals.

Lactate Reduction and ATP Depletion.

Figure 5A:
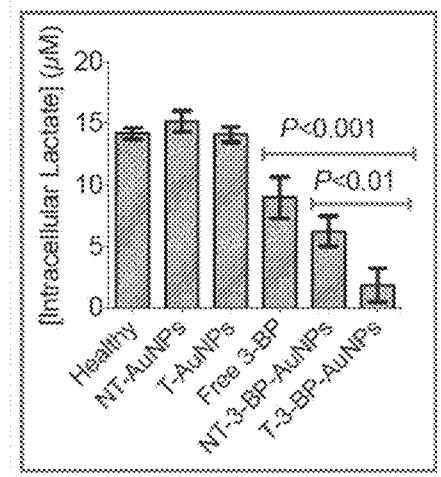
FIG. 5: Intracellular (A) and extracellular (B) lactate levels in PC3 cells after treatment with T-AuNP (1 mg/mL), NT-AuNP (1 mg/mL), T-3-BP-AuNP (14.1 µg/mL with respect to NP, 10 µM with respect to 3-BP), NT-3-BP-AuNP (13.7 µg/mL with respect to NP, 10 µM with respect to 3-BP), free 3-BP (10 µM) for 6 h at 37° C. (C) Changes in intracellular ATP content in PC3 cells after treatment with T-AuNP (1 mg/mL), NT-AuNP (1 mg/mL), T-3-BP-AuNP (14.1 µg/mL with respect to NP, 10 µM with respect to 3-BP), NT-3-BP-AuNP (13.7 µg/mL with respect to NP, 10 µM with respect to 3-BP), free 3-BP (10 µM) for 6 h at 37° C. in 5% CO2 atmosphere. Results are represented as mean±SD (n=3). Statistical analyses were performed by using one-way ANOVA with Tukey post hoc test.
Figure 5B:
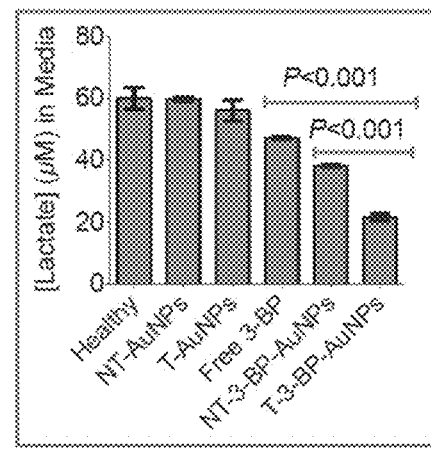
Figure 5C:
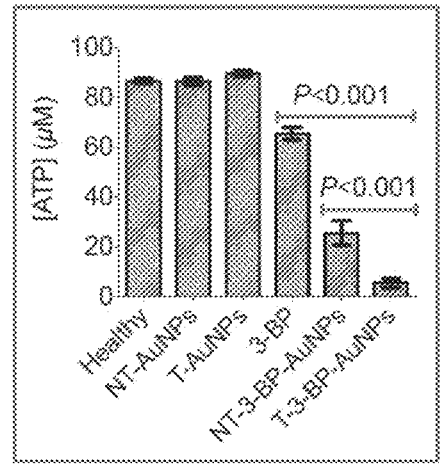
Figure 6A:
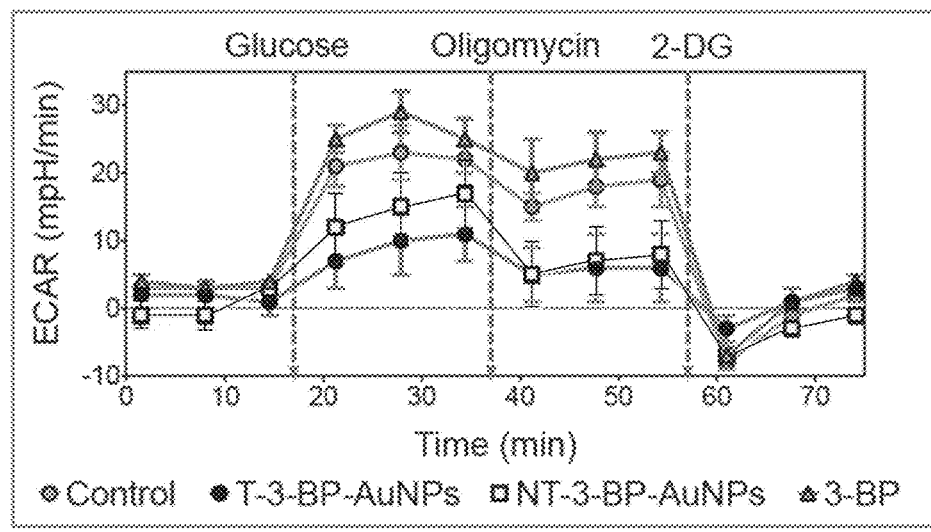
FIG. 6: Bioenergetics analyses in PC3 cell line. (A) A representative graph of ECAR output from XF24 analyzer of control, T-3-BP-AuNP, NT-3-BP-AuNP, and free 3-BP treated PC3 cells and its response to glucose, oligomycin, and 2-DG and (B) comparison of glycolysis, glycolytic capacity, and glycolytic reserve in the treated cells. (C) A representative graph of OCR output from XF24 analyzer of control, T-3-BP-AuNP, NT-3-BP-AuNP, and free 3-BP treated PC3 cells and its response to oligomycin, FCCP, antimycin A/rotenone and comparison of (D) spare respiratory capacity, coupling efficiency, and (E) ETC accelerator response and basal respiration in the treated cells.
Figure 6B:
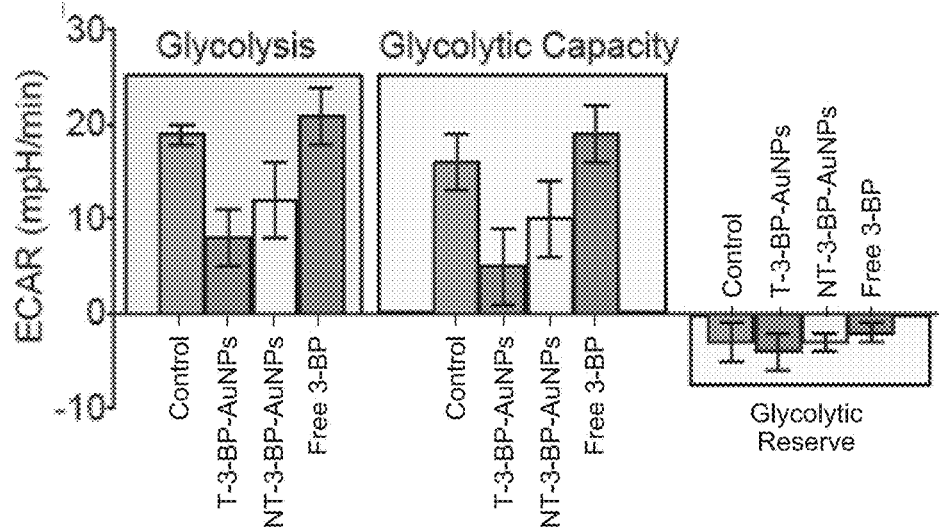
Figure 6C:
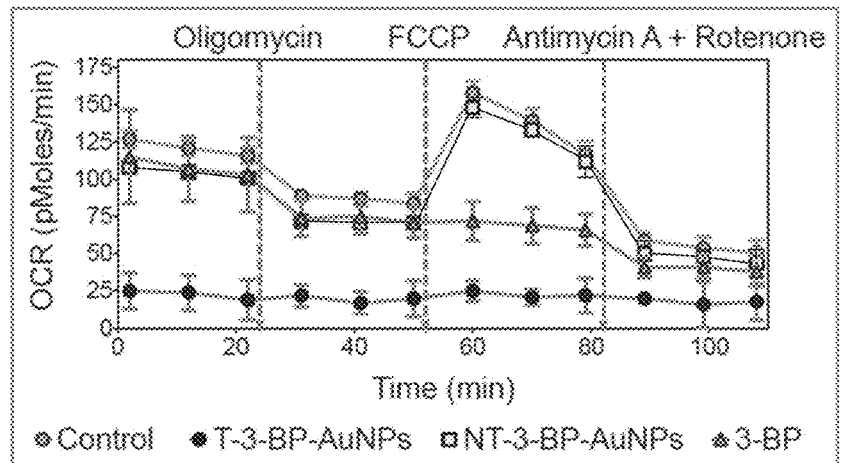
Figure 6D:
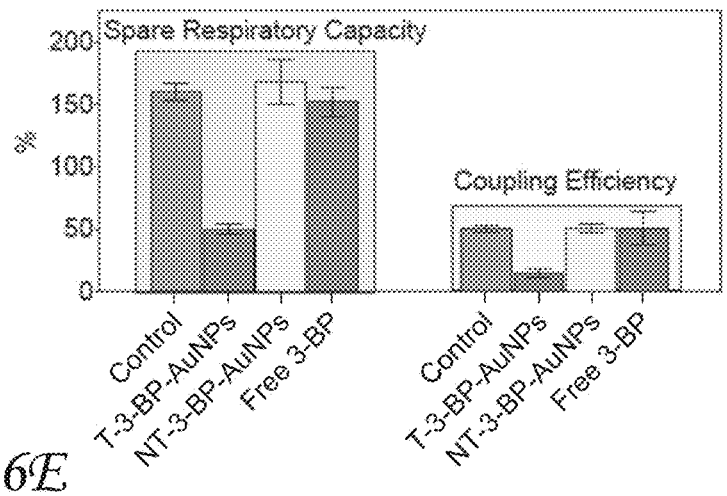
Figure 6E:
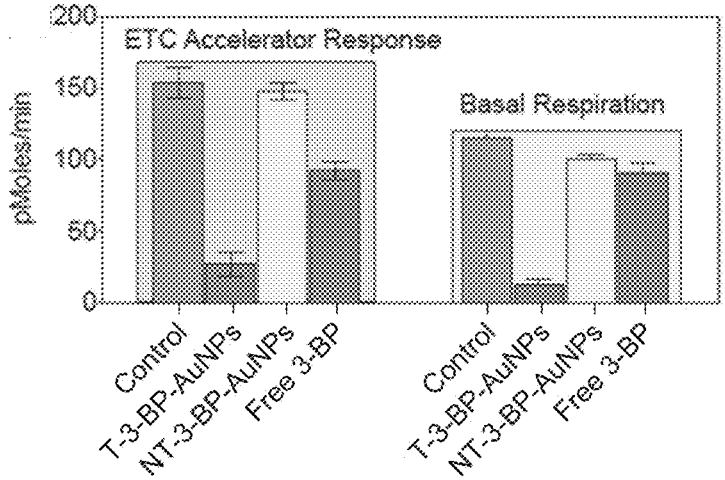

The final product of glycolysis is lactate. Hence, we quantified intracellular and extracellular lactate levels in PC3 cell lines treated with 3-BP, T-3-BP-AuNPs, NT-3-BP-AuNPs, T-AuNP, and NT-AuNPs. Extracellular lactate levels were found to be much higher than those observed in the cells (FIGS. 5A and 58B). Our results showed that the levels of both intracellular and extracellular lactate declined with treatment with free 3-BP, T-3-BP-AuNPs, and NT-3-BP-AuNPs. This decrease was more significant in cells which were treated with T-3-BP-AuNPs compared to the cells treated with either 3-BP or 3-BP conjugated to NT-AuNPs (FIGS. 5A and 5B). Treatment with T-3-BP-AuNPs, NT-3-BPAuNPs, and 3-BP showed a decrease in the level of ATP in PC3 cells (FIG. 5C). The PC3 cells were found to be much more sensitive to T-3-BP-AuNPs than free 3-BP or NT-3-BP-AuNPs as inferred from the intracellular ATP levels at 6 h (FIG. 5C). The present data showed T-3-BPAuNPs has the ability to show depletion of ATP and reduction in lactate levels at lower 3-BP concentrations compared to free 3-BP or NT-3-BP-AuNPs. These observations further supported the importance of delivering 3-BP to the mitochondria in modulation of its efficacy.

Perturbation of Bioenergetic Functions of PC3 Cells by T-3-BP-AuNPs.

We performed real-time measurements of extracellular acidification rate (ECAR), an indicator of glycolysis and oxygen consumption rate (OCR) which is a marker of OXPHOS in highly glycolytic PC3 cells after treatment with T-3-BP-AuNPs, NT-3-BP-AuNPs, and free 3-BP using a Seahorse XF24 extracellular flux analyzer (FIG. 6). Glycolytic parameters were calculated by monitoring changes in ECAR in response to sequential addition of D-glucose to assess glycolysis, oligomycin to measure maximal glycolytic capacity, and 2-deoxy-D-glucose (2-DG) as a measure of glycolytic reserve capacity (FIGS. 6A and 6B). Administration of excess of glucose to T-3-BP-AuNP treated PC3 cells in glucose-depleted medium showed only modest increase in the ECAR levels indicating remarkable activity of T-3-BP-AuNPs in glycolysis inhibition. Under similar conditions, 3-BP delivered by NT-AuNPs showed less efficiency in glycolysis inhibition and free 3-BP at this low concentration of 10 μM did not show any glycolysis inhibitory effect (FIG. 6A). Significant inhibition of glycolysis by T-3-BP-AuNPs in PC3 cells was further supported by sequential administration oligomycin and 2-DG, the cells treated with T-3-BPAuNPs did not show any significant changes in the ECAR levels. These data demonstrated remarkable ability of 3-BP at a low concentration of 10 μM in inhibition of glycolysis only when delivered with a mitochondria-targeted delivery system. We next assessed the effects of T-3-BPAuNPs on the mitochondrial OXPHOS pathway and compared the results when 3-BP was either delivered with a NT-AuNP or in the free form (FIGS. 6C-E). By following the changes in the OCR values (FIG. 6C) in response to oligomycin to give maximal glycolytic capacity, carbonyl cyanide 4-trifluoromethoxy-phenylhydrazone (FCCP), an uncoupling agent that allows maximum electron transport and therefore a measure of maximum OXPHOS respiration capacity, and a combination of mitochondrial complex III inhibitor antimycin A and mitochondrial complex I inhibitor rotenone that allow precise measurement of mitochondrial uncoupling, spare respiratory capacity, coupling efficiency, ETC accelerator response, and basal respiration (FIGS. 6D and 6E) were measured. Significant decrease in the OCR in the PC3 cells that were treated with T-3-BP-AuNPs was noted.

We believe that the origin of this reduction was due to the ability of T-3-BP-AuNPs to target mitochondria-bound HK2 leading to loss of the mitochondrial integrity. Free 3-BP however has no preference for mitochondrial and cytosolic HK2. NT-3-BP-AuNPs showed preference for cytosolic HK2 as shown by their ability to reduce glycolysis and induce apoptosis, however, NT-3-BP-AuNPs did not affect the overall mitochondrial integrity. T-3-BP-AuNPs suppressed basal levels of OXPHOS and affected the ability of cancer cells to upregulate OXPHOS in response to agents such as FCCP that uncouple the mitochondrial proton gradient from ATP production. The effect of T-3-BP-AuNPs on OXPHOS, at a low 3-BP concentration of 100 μM is an important finding because other non-mitochondrial effects of free 3-BP may account for its cytotoxic effect at least at high doses. We believe that T-3-BP-AuNPs do not exert its effects via a single molecular target within the mitochondrial respiratory chain, but through several collective disruptions that leads to impairment of OXPHOS.

Potential Intracellular Targets of 3-BP Using Mitochondria-Targeted Delivery System.

Figure 7:
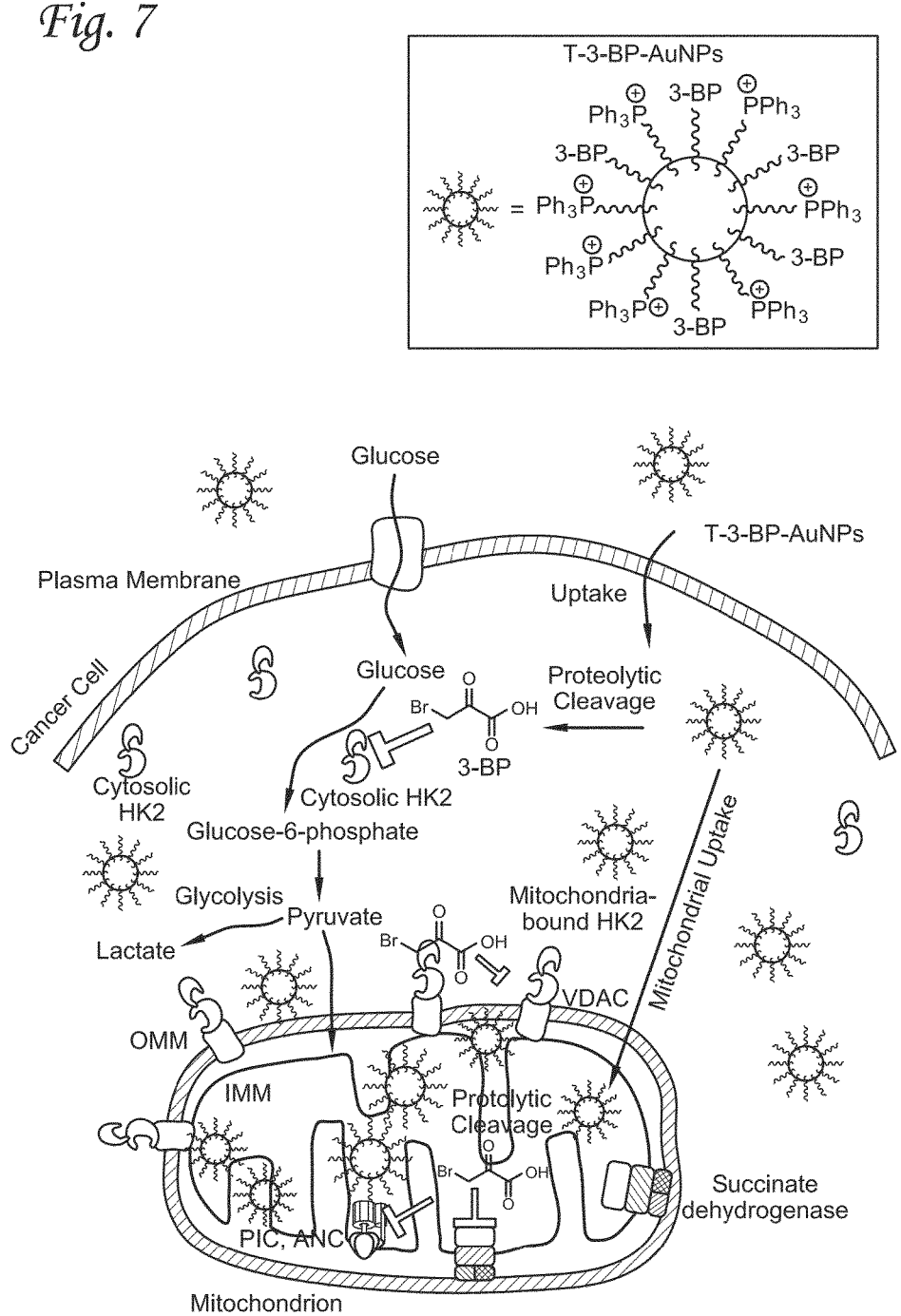
FIG. 7: Schematic drawing of various cellular targets and mechanism of action of 3-BP when it is delivered with a mitochondria-targeted delivery system.

Altogether, our data showed that T-3-BP-AuNPs have enormous potential in enhancing the efficacy of 3-BP. The overall mechanism of action of 3-BP when delivered with T-AuNP system is represented in FIG. 7. MCT is implicated as a 3-BP transporter and free 3-BP might not enter cells in the absence of MCT. When 3-BP is conjugated to a mitochondria-targeted NP system, as shown in T-3-BP-AuNPs, even in the absence of MCT or when MCT are engaged in cellular efflux of excess lactate in highly proliferative glycolytic cancers, T-3-BP-AuNPs with $\Delta\psi m$-targeted -TPP moieties will be taken up by cancer cells by utilizing the natural uptake mechanisms of AuNPs and the fact that cancer cells frequently have more negatively charged $\Delta\psi m$. Once inside the cells, a small portion of 3-BP released in the cytosol by the cytosolic proteases will inhibit cytosolic HK2. T-3-BP-AuNPs localized in the OMM at the early stage of trafficking will release 3-BP for potential dissociation of HK2 from VDAC thereby promoting cellular apoptosis. T-3-BP-NPs localized in the mitochondrial matrix will play significant roles in shutting down of mitochondrial OXPHOS by inhibiting succinate dehydrogenase and other enzymes such as PIC and ANC.

CONCLUSIONS

In conclusion, this study showed that 3-BP delivered by a mitochondria-targeted NP system has enormous potential in increasing the therapeutic window of free 3-BP. To the best of our knowledge, this is the first demonstration of engineering of such a NP system for mitochondrial delivery of 3-BP with superior efficacy. Furthermore, we demonstrated that mitochondrial compartmentalization of 3-BP when delivered with a T-AuNP system is time-dependent which utilizes different targets of 3-BP in the mitochondrial compartments further enhancing 3-BP activity. 3-BP released from T-AuNP by a protease mediated hydrolysis showed HK2 inhibition, anti-proliferative effects on highly glycolytic PC3 and DU145 cell lines, inhibited lactate production, complete inhibition of glycolysis, and blocked energy metabolism in these cells, finally triggered cell death and apoptosis. The efficiencies of all these activities were much higher compared to 3-BPs when delivered using a non-targeted NP system or the free formulation. Treatment-derived toxicity, cell-insensitivity to metabolic drugs such as free 3-BP, and lack of therapeutic selectivity are still the major issues in developing strategies leading to cancer cure. Given its ability to selectively deliver 3-BP inside mitochondria, T-3-BP-AuNPs could constitute a leading construct in the development of chemotherapeutics that target the unique neoplastic alterations of the cell glucose metabolism and up regulation of HK2. This study showed the potential that delivery of 3-BP using a mitochondria-targeted delivery system is an effective means of limiting systemic toxicity while enhancing efficacy thus providing new strategies for 3-BP therapy.

Thus, embodiments of MITOCHONDIRAL DELIVERY OF 3-BROMOPYRUVATE are disclosed. One skilled in the art will appreciate that the nanoparticles and methods described herein can be practiced with embodiments other than those disclosed. The disclosed embodiments are presented for purposes of illustration and not limitation.

What is claimed is:

1. A nanoparticle, comprising:
    a radiation excitable core;
    hexokinase-2 inhibitor attached to the radiation excitable core; and
    a mitochondrial targeting moiety attached to the radiation excitable core, wherein the mitochondrial targeting moiety comprises a lipophilic delocalized cation.

2. The nanoparticle according to claim 1, wherein the radiation excitable core comprises gold.

3. The nanoparticle according to claim 1, wherein the mitochondrial targeting moiety comprising the lipophilic delocalized cation comprises a moiety selected from the group consisting of a triphenyl phosphonium (TPP) moiety and a rhodamine cation.

4. The nanoparticle according to claim 1, wherein the mitochondrial targeting moiety comprising the lipophilic delocalized cation comprises a triphenyl phosphonium (TPP) moiety or a derivative thereof.

5. The nanoparticle according to claim 1, wherein the hexokinase-2 inhibitor is selected from the group consisting of 3-bromopyruvate, 2-deoxy-D-glucose, lonidamine, and combinations thereof.

6. A method for treating a patient at risk or suffering from cancer, comprising administering an effective amount of the nanoparticle according to claim 1 to the patient.

7. The method according to claim 6, wherein the cancer is prostate cancer.

8. The method according to claim 6, further comprising laser irradiating cells containing the nanoparticles after administering the nanoparticles to the patient to cause the radiation excitable core to heat.

9. A nanoparticle, comprising:
    a core comprising gold, silver, or a quantum dot;
    a hexokinase-2 inhibitor attached to the core; and
    a mitochondrial targeting moiety attached to the core, wherein the mitochondrial targeting moiety comprises a triphenyl phosphonium moiety or a rhodamine cation.

10. The nanoparticle of claim 9, wherein the core comprises gold.

11. The nanoparticle of claim 10, wherein the mitochondrial targeting moiety comprises a triphenyl phosphonium moiety.

12. The nanoparticle of claim 9, wherein the mitochondrial targeting moiety comprises a triphenyl phosphonium moiety.

13. The nanoparticle according to claim 9, wherein the hexokinase-2 inhibitor is selected from the group consisting of 3-bromopyruvate, 2-deoxy-D-glucose, and lonidamine.

14. The nanoparticle according to claim 10, wherein the hexokinase-2 inhibitor is selected from the group consisting of 3-bromopyruvate, 2-deoxy-D-glucose, and lonidamine.

15. The nanoparticle according to claim 11, wherein the hexokinase-2 inhibitor is selected from the group consisting of 3-bromopyruvate, 2-deoxy-D-glucose, and lonidamine.

16. The nanoparticle according to claim 12, wherein the hexokinase-2 inhibitor is selected from the group consisting of 3-bromopyruvate, 2-deoxy-D-glucose, and lonidamine.

* * * * *